United States Patent
Julien et al.

(10) Patent No.: US 10,159,574 B2
(45) Date of Patent: Dec. 25, 2018

(54) METHOD FOR CO-PROCESSING COMPONENTS IN A METAL INJECTION MOLDING PROCESS, AND COMPONENTS MADE VIA THE SAME

(75) Inventors: Benoit Julien, Montreal (CA); Mathieu Boisclair, Montreal (CA); Alexei Mourski, Montreal (CA)

(73) Assignees: Flextronics Global Services Canada Inc., Toronto (CA); Services Globaux Flextronics Canada Inc., Toronto (CA)

( * ) Notice: Subject to any disclaimer, the term of this patent is extended or adjusted under 35 U.S.C. 154(b) by 1280 days.

(21) Appl. No.: 13/318,072

(22) PCT Filed: Apr. 29, 2010

(86) PCT No.: PCT/CA2010/000689
§ 371 (c)(1),
(2), (4) Date: Feb. 15, 2012

(87) PCT Pub. No.: WO2010/124398
PCT Pub. Date: Nov. 4, 2010

(65) Prior Publication Data
US 2012/0136400 A1     May 31, 2012

Related U.S. Application Data

(60) Provisional application No. 61/173,708, filed on Apr. 29, 2009.

(51) Int. Cl.
*B22F 3/10* (2006.01)
*A61F 2/36* (2006.01)
(Continued)

(52) U.S. Cl.
CPC .............. *A61F 2/3609* (2013.01); *A61F 2/28* (2013.01); *B22F 3/1021* (2013.01); *B22F 3/225* (2013.01);
(Continued)

(58) Field of Classification Search
None
See application file for complete search history.

(56) References Cited

U.S. PATENT DOCUMENTS 4,542,539 A * 9/1985 Rowe, Jr. ............ A61F 2/30767
606/76
5,308,576 A 5/1994 Green et al.
(Continued)

FOREIGN PATENT DOCUMENTS

CA       2538049 A1      3/2005
CA       2573752 A1      7/2007
(Continued)

OTHER PUBLICATIONS

International Search Report dated Aug. 11, 2010, 5 pages.
(Continued)

*Primary Examiner* — Daniel J. Schleis
(74) *Attorney, Agent, or Firm* — Volpe and Koenig, P.C.

(57) ABSTRACT

A method comprising molding a first component from a first feedstock comprising a first material powder and a first binder, molding a second component from a second feedstock comprising a second material powder and a second binder, placing the first component and the second component in physical communication with each other in order to form an assembled component, removing the first binder and the second binder from the assembled component and performing a sintering operation on the assembled component so as to bond the first component and the second component together.

15 Claims, 8 Drawing Sheets

(51) Int. Cl.
  *A61F 2/28* (2006.01)
  *B22F 3/22* (2006.01)
  *B22F 7/06* (2006.01)
  *C22C 1/08* (2006.01)
  *A61F 2/30* (2006.01)

(52) U.S. Cl.
  CPC ............... *B22F 7/06* (2013.01); *C22C 1/08* (2013.01); *A61F 2/3094* (2013.01); *A61F 2002/30004* (2013.01); *A61F 2002/30011* (2013.01); *A61F 2002/30968* (2013.01); *A61F 2002/30975* (2013.01); *A61F 2002/3619* (2013.01); *A61F 2250/0014* (2013.01); *A61F 2250/0023* (2013.01); *A61F 2310/00011* (2013.01); *A61F 2310/00179* (2013.01); *B22F 3/1025* (2013.01)

(56) References Cited

U.S. PATENT DOCUMENTS

| | | | |
|---|---|---|---|
| 5,616,026 A | 4/1997 | Cash | |
| 5,769,884 A * | 6/1998 | Solovay | A61F 2/07 606/194 |
| 5,972,269 A | 10/1999 | Barros et al. | |
| 6,022,509 A | 2/2000 | Matthews et al. | |
| 6,551,551 B1 | 4/2003 | Gegel et al. | |
| 6,811,569 B1 * | 11/2004 | Afriat | A61F 2/34 623/22.24 |
| 6,908,486 B2 * | 6/2005 | Lewallen | A61F 2/34 623/22.21 |
| 7,578,851 B2 * | 8/2009 | Dong | C23C 28/028 623/22.21 |
| 8,556,981 B2 * | 10/2013 | Jones | A61F 2/30907 623/18.11 |
| 9,403,213 B2 * | 8/2016 | Lapszynski | A61F 2/30771 |
| 2001/0033039 A1 * | 10/2001 | Lauf et al. | 264/44 |
| 2002/0062154 A1 * | 5/2002 | Ayers | A61F 2/28 623/23.76 |
| 2008/0009953 A1 * | 1/2008 | Ling | A61F 2/34 623/22.21 |
| 2008/0269829 A1 | 10/2008 | Li et al. | |

FOREIGN PATENT DOCUMENTS

| | | |
|---|---|---|
| EP | 0820737 A2 | 1/1998 |
| EP | 1300209 A2 | 4/2003 |
| GB | 2448031 A | 10/2008 |
| WO | 2002/083188 A2 | 10/2002 |
| WO | 2007/005632 A1 | 1/2007 |
| WO | 2007/120822 A1 | 10/2007 |

OTHER PUBLICATIONS

Written Opinion of the International Searching Authority dated Aug. 11, 2010, 7 pages.
International Preliminary Report on Patentability issued by the International Bureau of WIPO dated Nov. 1, 2011, 8 pages.

* cited by examiner

METHOD FOR CO-PROCESSING COMPONENTS IN A METAL INJECTION MOLDING PROCESS, AND COMPONENTS MADE VIA THE SAME

CROSS REFERENCE TO RELATED APPLICATIONS

This application claims the benefit under 35 USC § 119(e) of U.S. provisional patent application Ser. No. 61/173,708 filed Apr. 29, 2009. The contents of the above-mentioned patent application are incorporated herein by reference.

FIELD OF THE INVENTION

The present invention relates to a method for creating complex shaped parts using a metal injection molding process, and specifically to a method that uses co-processing of two or more sub-components in order to form an integral assembled component.

BACKGROUND OF THE INVENTION

Metal injection molding (or MIM) is a relatively cost-effective manufacturing process used to produce parts or components with complex shapes from materials such as metals, metal alloys, ceramics, cemented carbides and cermets (ceramic-metal composites), among others. MIM may be used to produce metallic and/or ceramic components with more complex shapes than could be produced using traditional manufacturing techniques, such as pressed powder sintering, investment casting, turning and machining.

The typical MIM manufacturing process involves several steps generally starting with the formation of a feedstock, which is comprised of a metal or ceramic powder(s) combined with a binder to produce a homogenous mixture. This feedstock is then injected into a mold to produce a "green part" that takes the shape of the mold. Once formed, the green part is removed from the mold, allowed to rest for a period of time and is then "debound", meaning the binder is removed from the part to leave the material powder in the shape of the part. The debound part is then sintered at a high temperature to cause the particles of the material powder to partially melt, bond together and form the completed part. In certain circumstances, a finishing operation is then performed on the completed parts (such as electroplating), however, these finishing operations may be considered as being separate from the MIM manufacturing process.

A deficiency with the existing MIM manufacturing process is that it is not always possible to manufacture complex shaped parts having certain geometries or characteristics (such as those having a hollow center or a portion consisting of a material in a porous state).

In light of the above, it may be seen that there is a need in the industry for an improved MIM processing method that alleviates, at least in part, the deficiencies associated with existing. MIM manufacturing processes in order to make it easier to manufacture components having certain desired geometries.

SUMMARY OF THE INVENTION

In accordance with a first broad aspect, the present invention provides a medical component comprising a body portion formed of a metal material, the metal material having a density of less than 99% of a theoretical possible density for the metal material, wherein the body portion surrounds a void having a volume greater than 0.5 cm$^3$.

In accordance with a second broad aspect, the present invention provides a medical component comprising a body portion formed of a metal material, the metal material having a density of less than 99% of a theoretical possible density for the metal material. The body portion comprises an outer peripheral surface, an internal cavity and an entry passage extending from the outer peripheral surface to the internal cavity, wherein a cross sectional surface area of the entry passage is less than a cross sectional surface area of the internal cavity.

In accordance with another broad aspect, the present invention provides a medical component comprising a first portion formed of a first metal material, the first metal material having a density of less than 99% of a theoretical possible density, and a second portion formed of a second metal material, the second metal material being different from the first metal material, the second metal material having a density of less than 99% of a theoretical possible density. The first portion and the second portion are joined together at a region of interface, wherein the region of interface between the first portion and the second portion is substantially seamless.

In accordance with another broad aspect, the present invention provides a medical component comprising a first portion formed of a first metal material, the first metal material having a density of less than 99% of a theoretical possible density and a second portion formed of a second metal material, the second metal material having a density of less than 99% of a theoretical possible density. The medical component further comprising a longitudinal axis and a transversal axis, wherein the medical component comprises a gradation in density along at least one of the longitudinal axis and the transversal axis.

In accordance with another broad aspect, the present invention provides a medical component comprising a body portion formed from at least one metal material, the at least one metal material having a density of less than 99% of a theoretical possible density, wherein the body portion decreases in density from a peripheral surface of the body portion towards a center region of the body portion.

In accordance with another broad aspect, the present invention provides a method, comprising molding a first component from a first feedstock comprising a first material powder and a first binder, molding a second component from a second feedstock comprising a second material powder and a second binder, placing the first component and the second component in physical communication with each other in order to form an assembled component, removing the first binder and the second binder from the assembled component and performing a sintering operation on the assembled component so as to bond the first component and the second component together.

These and other aspects and features of the present invention will now become apparent to those of ordinary skill in the art upon review of the following description of specific embodiments of the invention and the accompanying drawings.

Other aspects and features of the present invention will become apparent to those ordinarily skilled in the art upon review of the following description of specific embodiments of the invention in conjunction with the accompanying figures.

DETAILED DESCRIPTION

In accordance with the present invention, three (3) methods are provided for manufacturing a component using metal injection molding (MIM), wherein an assembled component is formed by joining two sub-components together using co-processing techniques. Although these methods share certain processes and procedures, each method will be described separately.

Method 1

Figure 1:
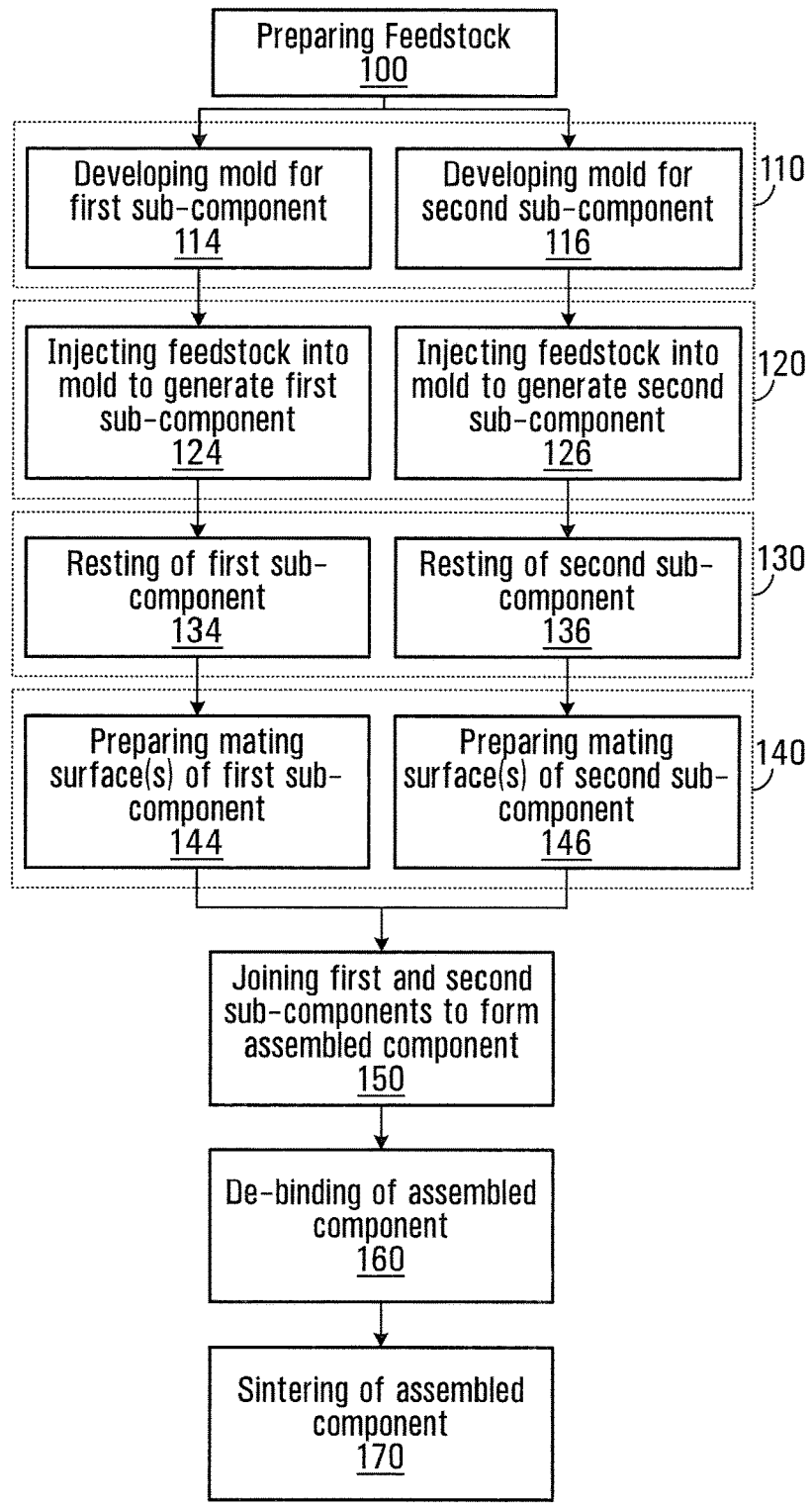
FIG. 1 shows a flow diagram of a first non-limiting co-processing method in accordance with a specific example of implementation of the present invention.

FIG. 1 shows a flow diagram of a first non-limiting co-processing method in accordance with a specific example of implementation of the present invention. As shown, the steps of the co-processing method involve preparing a feedstock for each of the sub-components that are to be joined together, injecting the feedstock(s) into respective molds for producing "green" parts for each of the sub-components, joining the sub-components together to form an assembled component, performing co-debinding for removing the binder from the assembled component while the components are in communication with each other and then sintering the assembled component to form the final assembled part. Further details for each of these steps will be described below, and an example showing the use of this method to produce an assembled component will also be described.

It should be understood that both the description and the example provided below refer to an assembled component that is formed by joining two (2) sub-components together. However, it should be appreciated that the present method is not limited to joining only two sub-components, and it may be used to form an assembled component that has any number of sub-components joined together.

Step 100

At step 100 of the method shown in FIG. 1, a feedstock material is prepared for each of the sub-components that are to be joined together. The feedstock is the material that is injected into a mold to take on the form defined by the mold cavity. The feedstock is generally a mixture of a base material powder and a binder. The base material powder will be the final material from which the sub-component is made, and the binder is an organic and/or inorganic material that is used to bind the powder together to form the feedstock.

Ideally, the feedstock that is produced by the base material powder and binder is homogeneous and predictable. The method for determining the quantities and types of material powder and binder needed to produce a predictable and homogenous feedstock are well known, and will not be explained in further detail herein.

As mentioned above, the base material powder portion of the feedstock is the material from which the sub-component will eventually be made. Non-limiting examples of base materials include stainless steel alloys, cobalt-chrome alloys, titanium alloys, alumina ceramics and cermets, as well as zirconia ceramics and cermets, among others. The base material is usually chosen depending on certain material properties/characteristics desired for the functionality of the sub-component, such as desired mechanical, chemical, and/or physical properties.

The binder portion of the feedstock is used to bind the powder of the base material together, thus allowing the material powder to be formed into a slurry that may be conveyed through injection equipment into an eventual mold. The binder may be a combination of organic and/or inorganic materials, which may be soluble or non-soluble. The binder may comprise a variety of waxes (such as bees wax and/or paraffin wax), dispersants and surfactants that confer certain properties to it, such as desired mechanical, chemical, and/or physical properties. In accordance with a non-limiting example, the feedstock is a wax-based feedstock with at least 75% wax that has a melting point below 60 degrees C.

In accordance with a non-limiting example, the binder used in the feedstock is organic and polymeric in nature, and may contain a mixture of polymers, such as polyethylene, polyethylene glycol (PEG), polymethyl methacrylate, and polypropylene, among others.

The process for selecting both a base material powder and an appropriate binder may be done in a variety of ways that will be known to a person of skill in the art, and as such will not be explained in further detail herein. In some cases, this selection process may be performed with the help of a software application that analyzes the specifications and desired characteristics for the finished part and makes recommendations as to the material powder and/or binder that would best meet these specifications and desired characteristics of the finished part.

Once the material powder and binder have been selected, a ratio of the selected material powder to binder (referred to here as the material powder-to-binder ratio) is developed to produce a homogenous and consistent feedstock with certain rheological properties. The process by which the material powder-to-binder ratio is determined will be known to those of skill in the art, and as such will not be explained in greater detail herein.

The two sub-components that are to be joined together using the method according to the present invention may be made from the same feedstock, or alternatively the two sub-components may be made from different feedstocks. As such, although step 100 is shown in a single block in FIG.

1, it could have been represented as two blocks with one block for each of two different feedstocks. In the case where the same feedstock is used for both sub-components, then only one feedstock needs to be prepared. However, in the case where the sub-components are made from different feedstocks, two different feedstocks will be prepared; namely one for each of the two sub-components. In this case, the two different feedstocks may be customized in order to provide different properties to each of the two sub-components that are to be joined together. For example, one sub-component may be constructed from a stainless steel alloy in order to provide corrosion resistance to a portion of the assembled component and the other sub-component may be constructed from a Zirconia-based ceramic to isolate the assembled component against electrical conductance. As such, in this example, the feedstocks from which the two sub-components are made are formulated with consideration for the functionality and specifications of each of the sub-components.

The feedstocks used to produce the at least two sub-components may also take into account that the two sub-components should behave similarly during debinding and sintering. More specifically, it is generally desirable that the two sub-components that are being joined together can be sintered at approximately the same temperature, and behave in the same manner during sintering (i.e. that they exhibit approximately the same metallurgical kinetics, such as shrinkage). This will help to ensure that the two sub-components shrink at approximately the same rate during sintering, which will help to form a stronger bond and avoid delamination between the two sub-components during sintering.

Those skilled in the art will appreciate that certain adjustment techniques may be employed when formulating the feedstock(s) for the different sub-components so that the sub-components behave similarly during the debinding and sintering phases of the MIM manufacturing process. For example, these adjustment techniques may include:

- adjusting the particle size of the material powder to adjust the manner in which the components respond to the sintering step; it is desirable that the sub components shrink in unison in order to avoid delamination at the interface caused by different shrinkage kinetics associated with the different materials; and/or
- using similar binder formulations in the feedstock for each sub-component to allow ease of co-debinding.

As will be mentioned in more detail below, during the sintering phase of the MIM manufacturing process, heat is applied to a component for causing the powder particles of the base material to melt sufficiently to bond together in order to form the finished part. During this process, the component may also experience a certain amount of shrinkage as the powder particles bond together. As such, when two sub-components are joined together, the materials from which the two sub-components are made, should behave in substantially the same manner during sintering. In particular, both of the materials from which the two sub-components are made should melt at approximately the same temperature, and at approximately the same rate, such that the two components shrink (which in some cases increases their density) at roughly the same rate when exposed to a given temperature. This helps to ensure the integrity and strength of the joint between the two joined sub-components.

If the powder particles, and the solid state diffusion characteristics which cause the densification of the base materials, do not react at approximately the same temperature, it is possible that one of the sub-component may shrink at a faster or slower rate than other sub-components, which could cause delamination and poor interface properties between the sub-components. This delamination may prevent a strong bond from being established or maintained between the sub-components.

Furthermore, under sufficient stress, it is possible that the joint between the two sub-components could delaminate, resulting in a possible loss of strength along the joining interface as well as the potential separation of the assembled component. To avoid this result, the sintering temperature (i.e., the temperature to which the assembled component is exposed) and the shrinkage rate of all joined sub-components should be approximately the same.

The possibility of each sub-component undergoing a different rate of shrinkage at a given sintering temperature increases if the two sub-components are created from different feedstocks, since each base material may react and shrink differently. In the case where the two sub-components are made from different feedstocks, the particle sizes of the material powder in the feedstock(s) may be adjusted in order to make the rate of shrinkage between the at least two sub-components approximately the same given the sintering conditions being applied.

The temperature at which a material powder will sinter and bond together may depend on the size of the powder particles of the base material. Therefore, one adjustment technique that may be used to make sub-components having different base materials sinter and shrink in approximately the same manner during sintering, is to adjust the particle sizes of the base material powder.

In general, decreasing the particle size of a material powder in a feedstock may cause a sub-component formed from this material powder to sinter at a lower temperature than if it was made of the same material powder having a larger particle size.

By adjusting the particle size of the powder material of two different sub-components, the materials of the two sub-components may be made to sinter at approximately the same temperature. In particular, the particle size of the material powder used in the feedstock to form at least one of the sub-components may be increased or decreased to adjust the temperature at which the particles of the material powder begin to sinter. By adjusting the particle size of the powders of the base materials, the rate at which the two parts shrink may also be made to be approximately the same.

When the shrinkage rate for the joined sub-components is approximately the same, it is likely that the assembled component as a whole will shrink in a standard and predictable way, thus reducing stress that would otherwise be applied to the joining surfaces between the sub-components.

In the case where two different base materials are being used for two different sub-components, the feedstocks that form these two sub-components may be adjusted in order to ensure that their binders are the same as well. This facilitates the debinding process since the binder may be removed from both of the sub-components substantially simultaneously. Although this technique may be employed during feedstock formulation, the effect of its usage will be described in more depth within the context of the debinding process, described below.

Step 110

At step 110, molds for each of the individual sub-components are developed and prepared. While FIG. 1 shows step 110 occurring after the feedstock has been formulated (step 100), it is possible that two these steps may occur simultaneously or be reversed. For example, it is possible that the molds are developed and prepared prior to the formulation of the one or more feedstocks. In some embodiments, the rheological properties of the feedstock and the characteristics of the mold are considered together in order to determine the optimal molding conditions (e.g., feedstock temperature, pressure and duration for injection to the mold, etc.) for a sub-component.

In the non-limiting example shown in FIG. 1, step 110 is represented by two boxes, 114 and 116, each representing the respective development and preparation of a mold for one of the sub-components.

The molds for the sub-components may be made from a variety of metallic materials (e.g., steel, aluminum, bronze, brass), polymeric materials (e.g., epoxy resin, silicon) or thermoplastic material (e.g., ABS plastic). The molds are developed and prepared such that they define an interior cavity having the shape of the desired sub-components.

The molds used to form the sub-components may include markings and/or contain other features designed to impart "reference features" to the sub-components. The term "reference feature" is used herein to refer to certain physical markings on, or features of, a sub-component that are intended to indicate how the at least two sub-components should be oriented, positioned and/or brought into physical contact with each other to form the assembled component. For example, the reference features may include certain guide markings (e.g., lines or arrows), extrusions/notches, cavities/grooves and/or attachments for a jig, among other possibilities. These features are typically added to the mold so that they are integrated into the green part for the sub-component that is formed from that mold.

Reference features may help orient sub-components in relation to each other before they are joined, as well as provide ways to check that sub-components are correctly aligned. For example, molds for two sub-components may include guide arrows that become lined up with each other when the two sub-components are oriented properly for attachment.

In general, the reference features will be positioned in proximity to one or more "mating surfaces". The term "mating surface" is used herein to refer to the physical surfaces of a sub-component that come into physical contact with the mating surfaces of one or more other sub-components, in order to join the sub-components together.

Since the processes and techniques for developing MIM-related molds are believed to be well known to persons of skill in the art, further explanation of this step will not be provided herein.

Step 120

At step 120, the feedstock, or feedstocks, are injected into the molds that were prepared during step 110. During step 120, the feedstock for each of the at least two sub-components is injected into a respective mold so that the feedstock may assume the shape of the mold. In the embodiment shown in FIG. 1, this step is represented by two boxes, 124 and 126, each of which represents the injection of feedstock into a respective mold for one of the sub-components.

The one or more feedstocks are injected into their respective molds at a specified temperature, pressure and injection rate, depending on the rheological characteristics of the feedstock, as well as any predetermined molding conditions. Typically, the injection temperature and pressure are kept constant during feedstock injection into the mold in order to avoid the formation of cracks or voids within the formed feedstock. Once the feedstock has been injected into the mold, the resulting shape acquired by the feedstock from the mold is referred to as a "green part."

In accordance with a non-limiting example of implementation, a low pressure injection molding process is used to inject the feedstocks into their respective molds, which involves injecting the feedstocks into the molds at a pressure of less than 80 psi and at a temperature of below 80 degrees C.

The process for injecting feedstock into a mold and generating green parts in a MIM manufacturing process is believed to be well known by persons of skill in the art, and as such, no further explanation of this step is provided herein.

Step 130

At step 130, the green parts for each sub-component are removed from their respective molds, and then undergo a resting period. In FIG. 1, this step is represented by two boxes, 134 and 136, each of which represents the resting period for one of the green parts formed for each of the sub-components.

The resting periods allow the formed feedstock within the green parts to settle into the new molded shape so as to eliminate any residual stresses that may have been introduced during injection. These residual stresses could cause unexpected deformation during debinding and/or sintering of the sub-component. In addition, the resting period is used to reduce any residual stresses that might otherwise add stress to the joint(s) formed between the mating surfaces of assembled sub-components, thereby reducing the likelihood of the assembled component delaminating due to such stresses.

The resting period for a green sub-component may vary depending on a variety of factors. For example, the length of the resting period may depend on the material powder used for the sub-component, the rheological properties of the feedstock and/or the physical profile of the sub-component, among others. While these factors may be used to determine the length of the resting period, it should be appreciated that the length of the resting period may also be determined in a more approximate manner based on prior experience. As it is believed that a person of skill in the art will be able to determine an appropriate resting period for the green parts, further explanation of this step need not be provided.

Step 140

At step 140, the mating surfaces of the two sub-components are prepared for assembly. In the embodiment shown in FIG. 1, this step is represented by two boxes, 144 and 146, each of which represents the preparation of one of the sub-components to be joined.

The preparation of the mating surfaces may involve a plurality of different operations. For example, one of these preparation operations may involve removing any "flashing" from the mating surface. Flashing refers to excess feedstock material that may have accumulated on the parts during the molding operation. Removal of the flashing from the mating surfaces (as well as from other surfaces of the sub-component) may be necessary to ensure proper physical contact between the mating surfaces of sub-components when they are joined together.

Another preparation operation may involve treating the mating surfaces of the sub-components with a bonding agent. A "bonding agent" generally refers to a compound that forms a miscible solution with the mating surface so as to allow a bond to be created between it and the mating surface of another sub-component when they are physically joined together. In this respect, the bonding agent acts as a type of glue that at least temporarily holds the two mating surfaces (and by extension, their sub-components) together.

The bonding agent may be any compound that is suitable for at least temporarily holding the at least two sub-components together. In accordance with a non-limiting embodiment, the composition of the bonding agent that is applied to the at least two sub-components may be related to the composition of the feedstock(s) of the sub-components, and in particular, to the composition of the sub-components' binder(s). It should be noted that the bonding agent temporarily holds the at least two sub-components together prior to debinding and sintering, and is not necessarily meant to remain within the final part or component. Therefore, in some circumstances, it is possible that the bonding agent is removed from the assembled component during debinding and/or sintering operations. By relating the bonding agent to the binder (such as through a physical or chemical relationship), the bonding agent may be simultaneously removed with the binder from the assembled component during debinding or sintering.

In a first non-limiting example, the bonding agent may be a polymeric bonding agent that interacts with the feedstock(s) of the sub-components, and in particular, with the binder(s) within the feedstocks. For example, in the case where the binder is a polymeric binder (e.g., PEG, polypropylene, polyethylene), it may be desirable that the polymeric bonding agent has a molecular weight that is less than the molecular weight of the binder and be in the liquid state for application (example Molecular weight of PEG in binder is 105 which is solid at room temperature and molecular weight of PEG used as a bonding agent be 300 which is liquid at room temperature for the bonding operations). In such a case, the polymers within the bonding agent will tend to be more compatible to the polymers of equal or higher molecular weights in the binder, which allows the sub-components to be held together, at least temporarily.

In a second non-limiting example, the bonding agent may be a non-polymeric bonding agent. For example, in the case where the binder does not contain polymeric elements, a compound such as oleic acid may be used as the bonding agent. Oleic acid may be attracted to, or interact with elements in the binders of the at least two sub-components in order to attract them to each other, which allows the sub-components to be held together, at least temporarily.

The bonding agent that is applied to the mating surfaces of the sub-components may be in liquid form, which is easy to apply to the surfaces to be joined. For example, the bonding agent may be applied to the mating surface(s) of each sub-component using a brush or similar applicator. It should also be appreciated that the application of the bonding agent to the mating surfaces should be performed with care, as any bonding agent applied to non-mating surfaces will likely be visible once the assembled component is sintered and/or finished.

A certain amount of material powder may optionally be added to a bonding agent before application to the mating surfaces of the sub-components. This extra material powder then remains after the binder and the bonding agent are removed from the assembled component, which may strengthen the joint(s) between sub-components during sintering.

Step 150

At step 150, the mating surfaces of the at least two sub-components are placed into physical contact with each other in order to form the assembled component. When joining the mating surfaces together, the orientation of the sub-components may be determined based on their geometry, or based on any reference features they may have, which were described above.

In certain cases, the geometry of the component is sufficient to show how the mating surfaces of the sub-components should be joined together. For example, the general geometry of an assembled spherical component is likely to provide enough information to allow the assembly of two hemispherical sub-components along their mating surfaces.

Mating surfaces for each of the at least two sub-components may also be aligned, oriented and joined together using reference features integrated within each of the sub-components. For example, a guide arrow or similar marking could show the location of the mating surfaces, as well as indicate how these surfaces should be aligned with each other in order for successful formation of the assembled component. For example, the guide arrows used to identify mating surfaces for a sub-component may become lined up with similar arrows on another sub-component when the two sub-components are oriented properly with respect to each other.

Alternatively, the mating surfaces may be an integral part of the reference features, such as where the reference features for sub-components include a groove and projection. For example, assume that two sub-components are to be joined, whereby a first sub-component has a groove that is designed to accommodate a projection that extrudes from a second sub-component. In this case, the mating surfaces are located on the interior surface of the groove and on the exterior surface of the extrusion. These mating surfaces come into physical contact when their reference features are properly oriented to allow their respective sub-components to be joined together.

It is also possible that the formation of the assembled component may need to be performed with a more precise orientation and alignment of the at least two sub-components than may be possible manually. In such a case, the reference features may include attachments for a jig or tool to which the at least two sub-components may be attached and which orients their mating surfaces for joining.

In addition, it should be understood that although step 150 is presented as a single step, it may be possible that the formation of the assembled component may require multiple iterations of the orientation, alignment and joining of the at least two sub-components.

Step 160

At step 160, a co-debinding operation is performed on the two sub-components that have been joined together to form the assembled component. The term co-debinding is used to refer to the process of removing the binder from both the first sub-component and the second sub-component while the two sub-components are joined together. During this step, the binder, and in some cases the bonding agent, are removed from the at least two joined sub-components, leaving the material powder within the form of the assembled component.

Debinding techniques that may be used for co-debinding may include solvent debinding to remove soluble binders/bonding agents (e.g., PEG) and thermal wick debinding to remove non-soluble binders/bonding agents (e.g., polypropylene). Since the techniques used to debind components produced using the MIM manufacturing process are believed to be well known, further explanation of this step need not be provided.

In accordance with a first non-limiting embodiment, the at least two sub-components may be simultaneously co-debound using a single debinding technique. For example, when the feedstocks of all sub-components share the same binder material and bonding agent, a single debinding technique may be used. For example, in the case where the feedstocks of the sub-components use a water-soluble polymer as the binder and bonding agent (e.g., a high molecular weight version of PEG for the binder and a low molecular weight version of PEG for the bonding agent), a water debinding technique may be employed to co-debind the assembled component. In this technique, the assembled component may be immersed in wafer for a period of time to remove the PEG binder and bonding agent from the joined sub-components. Alternatively, in the case where the feedstocks of the sub-components use a non-water soluble polymer as the binder and/or bonding agent, a thermal debinding process may be used. Thermal debinding may also be referred to as wick debinding.

In a second non-limiting example, a single debinding technique (such as water debinding or wick debinding) may be used even when the feedstocks of the sub-components use different binder elements and/or bonding agents, so long as the different binder elements and/or bonding agents may be removed using the same debinding technique. For example, in the case where the feedstock of a first sub-component contains paraffin wax and a second sub-component contains bees wax, a thermal debinding technique may be used to co-debind the assembled component simultaneously. In this technique, the assembled component is placed within a wicking media (such as high purity alumina powder) and then heated within a furnace or oven in order to melt the wax-based binders and co-debind the joined sub-components. As the wax binders melt and flow out of the joined sub-components, they are absorbed and retained by the wicking media.

In a third non-limiting example, a plurality of different debinding techniques may be used during the co-debinding step. For example, in the case where the feedstocks of the sub-components contain different binder elements and/or bonding agents, these different binder elements and/or bonding agents may need to be extracted using different debinding techniques. For example, if the binder of a first sub-component includes water-soluble PEG and the binder of a second sub-component includes non-soluble polypropylene, both water debinding and thermal debinding techniques may need to be employed in order to co-debind the joined sub-components. In this case, the assembled component may first be immersed in water to remove the PEG binder from the first sub-component via water-debinding. The partially co-debound assembled component may then be transferred to a container containing a wicking media that is placed in a furnace or oven, which is then heated to extract the polypropylene binder from the second sub-component via thermal debinding.

One of the adjustment techniques described earlier in the context of tailoring the feedstocks for the sub-components in order to account for the fact that they will be joined together, was to use a similar binder formulation in the respective feedstocks. In general, by using the same or similar binder within the one or more feedstocks that are used to form the sub-components, a single debinding technique may be used to co-debind the assembled component. This obviously facilitates the co-debinding process. More specifically, by using a single debinding technique to remove the binder (and bonding agent) from the at least two joined sub-components, the amount of time and resources needed to co-debind the assembled component may be reduced.

In accordance with a non-limiting example of implementation, a thermal wick debinding process can be used to remove the binder. The thermal wick debinding is performed until the assembled component is pre-sintered, which generally means exposing the assembly to a temperature in the range of 45% to 65% of the melting point of the material. Solvent debinding may be used in the case where there are sufficient backbone polymers in the feedstocks (5%, and up to 10-20%).

Step 170

At step 170, once the binder has been removed from the assembled component, the assembled component is sintered in an oven or furnace at a temperature that is high enough to cause the particles of material powder in the at least two joined sub-components to at least partially melt and bond together, thus increasing the density and decreasing the porosity of the assembled component.

The sintering of an assembled component is performed using a "sintering profile" that identifies the temperature, pressure and atmospheric conditions to which the assembled component is exposed during the sintering operation. The purpose of the sintering profile is to provide sintering conditions that allow for the shrinkage of a component to occur in a substantially standard and predictable way as its material particles at least partially melt and bond together. As a result, the sintering profile typically includes a certain sintering temperature as well as a "ramp rate" that indicates how quickly sintering conditions (such as an oven's temperature) should be increased or decreased to encourage such standard and predicable shrinkage. Since the techniques used to develop sintering profiles and sinter MIM-produced components are well known to those who are skilled in the art, further explanation of this step need not be provided herein.

In the case of the assembled component, the sintering profile should take into account the fact that the rate of shrinkage should be approximately the same for all of the sub-components to achieve consistent and predictable shrinkage for the component as a whole. This helps to avoid delamination. It may be recalled that one of the adjustment techniques described earlier was to adjust the particle size of the material powder in the feedstock to ensure that the melting of the material of the sub-components during sintering was approximately the same. By implementing this technique and implementing an appropriate sintering profile, the shrinkage rate for the joined sub-components may be made to be approximately the same, thus increasing the likelihood that the assembled component as a whole will shrink in a standard and predictable way and avoid delaminating at the joint(s) between the sub-components.

The sintering profile may be used to reliably sinter an assembled component whose joined sub-components may be made from the same base materials or from different base materials while ensuring that the assembled component is likely to shrink in a substantially uniform, standard and predictable way.

Those skilled in the art will appreciate that the method described above for joining multiple sub-components together to form an assembled component allows the assembled component to have a more complex net shape than could be produced by molding an individual part.

In addition, it should be noted that this method allows parts with complex net shapes, and hollow components to be made. This may be useful in many industries, including the medical equipment industry.

As mentioned above, this method may be used to produce parts or components that have a hollow interior, which may be difficult to produce using other manufacturing methods. For example, two sub-components with interior central hemispherical voids may be joined and co-debound using the above method to create an assembled component having a hollow interior.

In certain cases, it may be desirable to design a part or component with a hollow interior, especially when the weight of the part or component is of concern. For example, the weight of a medical implant used for joint replacement surgeries (such as an implant for hip or knee replacement) has an impact on the ability of the patient to regain their original range of motion and restore their mobility. Therefore, it may be beneficial to reduce the weight of such components as much as possible through the use of lightweight materials, as well as through the design of components with hollow interiors.

In accordance with a first non-limiting example, the above-described method can be used in order to manufacture a medical component that has a hollow void therein. As will be described in more detail below, the medical component may be a surgical implant, such as a hip implant, or other orthopaedic implant. The medical component could also be a surgical tool or a cutting guide, among other possibilities.

The medical component is formed of at least two sub-components that when placed together along their mating surfaces, create a hollow void within the assembled component. As such, once debound and sintered, the medical component comprises a body portion that surrounds a hollow void.

The body portion is formed from the two metallic sub-components that are formed via the metal injection molding process described above. As such, once debound and sintered, the assembled body portion of the medical component is formed of a metal material. The metal material may include stainless steel alloys, cobalt-chrome alloys, titanium, titanium alloys, alumina ceramics and cermets, as well as zirconia ceramics and cermets, among other possibilities. Given that the body portion is formed from an assembly of two-subcomponents that are formed via the metal injection molding process described above, the body portion has a density of less than 99% of a theoretical possible density, which would be the density of the metal in its pure form. More specifically, once the assembled medical component has been de-bound and sintered, small porosities remain within the finished component as a result of the removal of the binder material, thus making the finished component less dense than the same metal material would be if it was in a pure block form.

The following is a non-limiting example of a method for measuring the density of a component formed from the metal injection moulding process described above. The density can be evaluated using Archimedes technique, wherein a part is weighed dry and is then weighed again when suspended in water. The difference in weights is due to a buoyant force created by the porosities. This difference in the two weights enables the calculation of density according to the following equation: DENSITY=(dry mass*density of water)/(dry mass−wet mass).

The following is a specific manner in which density is calculated:
Step 1—A sample of the component is taken. The sample can be cut using a slow-cutting saw;
Step 2—The dry sample is weighed using a measuring scale;
Step 3—The sample is then suspended within a body of liquid, and the weight of the suspended sample is taken;
Step 4—The density of the component is determined by entering the dry weight and the weight when suspended in water into the formula DENSITY=(dry mass*density of water)/(dry mass−wet mass). The density can be calculated manually or using a computer program.

Density measurements by the Archimedes technique are ASTM B328 (which is a standard test method for density, oil content and interconnected porosity of sintered metal structural parts) and ASTM B311 of MPIF std. 42.

As mentioned above, the body portion of the assembled medical component surrounds a hollow void. The hollow void may be substantially spherical in shape, or may be of any shape or configuration desirable. The shape of the hollow void will be defined by the shapes of recesses formed in the sub-components that are joined together. In general, the hollow void will have a volume greater than 0.5 cm$^3$.

In accordance with a second non-limiting example, the above-described method can be used in order to manufacture a metal component that has an internal cavity with an access passage that leads into the internal cavity. More specifically, the internal cavity has a smaller cross sectional area than a cross sectional area of the internal cavity. Shown in FIGS. 2 and 3 is a non-limiting example of a heat sink 400 that is manufactured according to the co-processing method described above.

Figure 2:
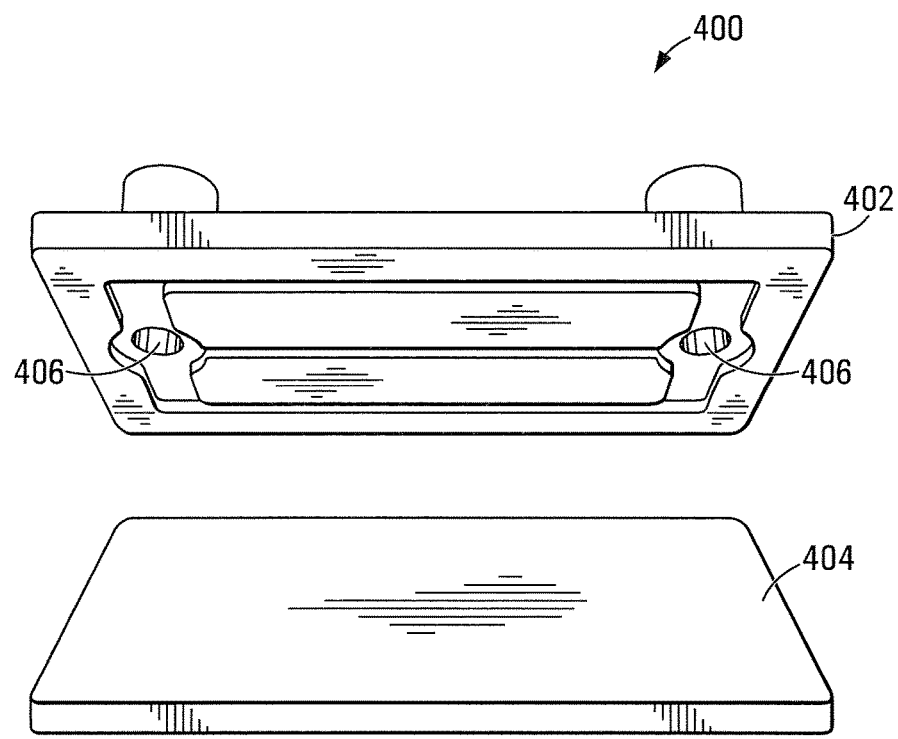
FIG. 2 shows a front perspective view of two non-limiting sub-components, prior to the two sub-components being joined together to form an assembled component.
Figure 3:
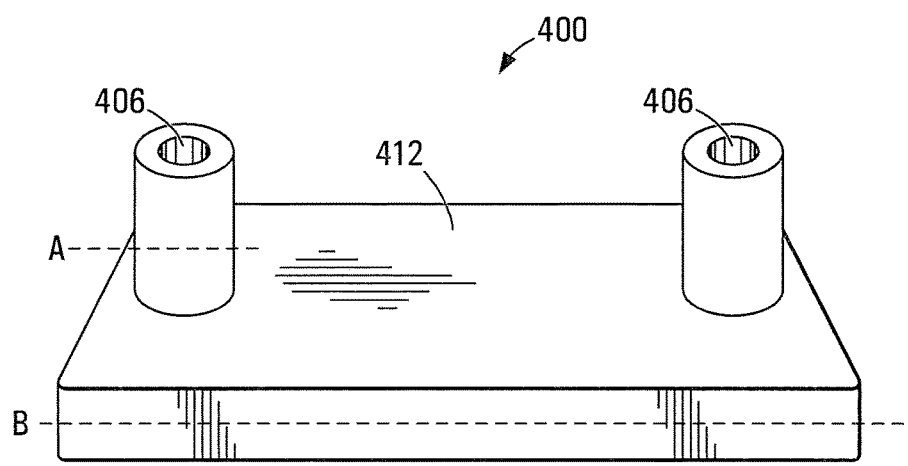
FIG. 3 shows a front perspective view of the two non-limiting sub-components of FIG. 2 shown in an assembled component.

Shown in FIG. 2 are two sub-components 402 and 404 that are eventually joined together in order to form the assembled heat sink 400. As shown, the first sub-component 402 comprises a plate like structure that has an internal cavity 408 and two access passages 406 that lead to the internal cavity 408. Once the first sub-component 402 and the second sub-component 404 have been joined together, debound and sintered together, they form the assembled heat sink 400 as shown in FIG. 3.

The heat sink 400 is formed of a metal material, that may include stainless steel alloys or copper alloys among other possibilities. In the same manner as described above, given that the heat sink 400 is formed from two-subcomponents 402 & 404 that are formed via a metal injection molding process, once the binder has been removed from the two sub-components 402 & 404 and they have been sintered together, the removal of the binder material leaves small porosities within the finished component. As such, the assembled heat sink 400 is less dense than it would be if it was made from the same metal material in a pure block form. In accordance with a non-limiting embodiment, the metal component has a density of less than 99% of a theoretical possible density, which would be the density of the same metal material in its pure form.

The assembled heat sink 400 comprises an outer peripheral surface 412, and two access passages 406 that lead towards the internal cavity 408 that is formed between the first and second sub-components 402 & 404. By using the MIM co-processing method as described above, the assembled component can include internal structures that would not be possible by machining or simple injection molding techniques. More specifically, and as explained with respect to the heat sink 400 shown in FIGS. 2 & 3, the assembled component 400 comprises an internal cavity 408 that has a greater cross-sectional surface area than that of an entry passage 406 leading from the peripheral surface 412 to the internal cavity 408. With reference to FIG. 3, the cross sectional surface area of the entry passage 406, as taken along plane A, would be smaller than the cross sectional surface area of the internal cavity 408, as taken along plane B.

Although FIGS. 2 and 3 show a heat sink 400, it should be appreciated that the same concept of having an internal cavity 408 with a greater cross sectional surface area than that of an access passage 406 leading to the internal cavity 408, can also be applied to medical components. The medical component may be a surgical implant, such as a hip implant, or other orthopaedic implant. The medical component could also be a surgical tool or a cutting guide, among other possibilities.

With further reference to FIG. 3, the first sub-component and the second sub-component are joined together at a region of interface (which in FIG. 3 is the region in proximity to where the line of plane B is shown). The region of interface is located in the vicinity of where the mating surfaces of two sub-components are joined together. By performing co-debinding of the two sub-components and then sintering the sub-components together, the region of interface between the first sub-component and the second sub-component is substantially seamless.

It is also possible that when the first sub-component and the second sub-component are formed of two different metal materials, when they are joined together, the region of interface between the first sub-component and the second sub-component is substantially seamless to the touch. However, due to the material characteristics of the different materials, it is possible that there is a visible seam.

Method I Example I—A Hip-Rotator Implant

The following is a more detailed example of a medical component that can be produced using the above-described co-processing method. For the sake of example, the medical component that will be described will be a surgical implant in the form of a hip implant. However, it should be appreciated that any other medical component, such as a surgical tool, cutting guide, or other orthopaedic implant could be made via the present co-processing method, without departing from the spirit of the invention.

Figure 4:
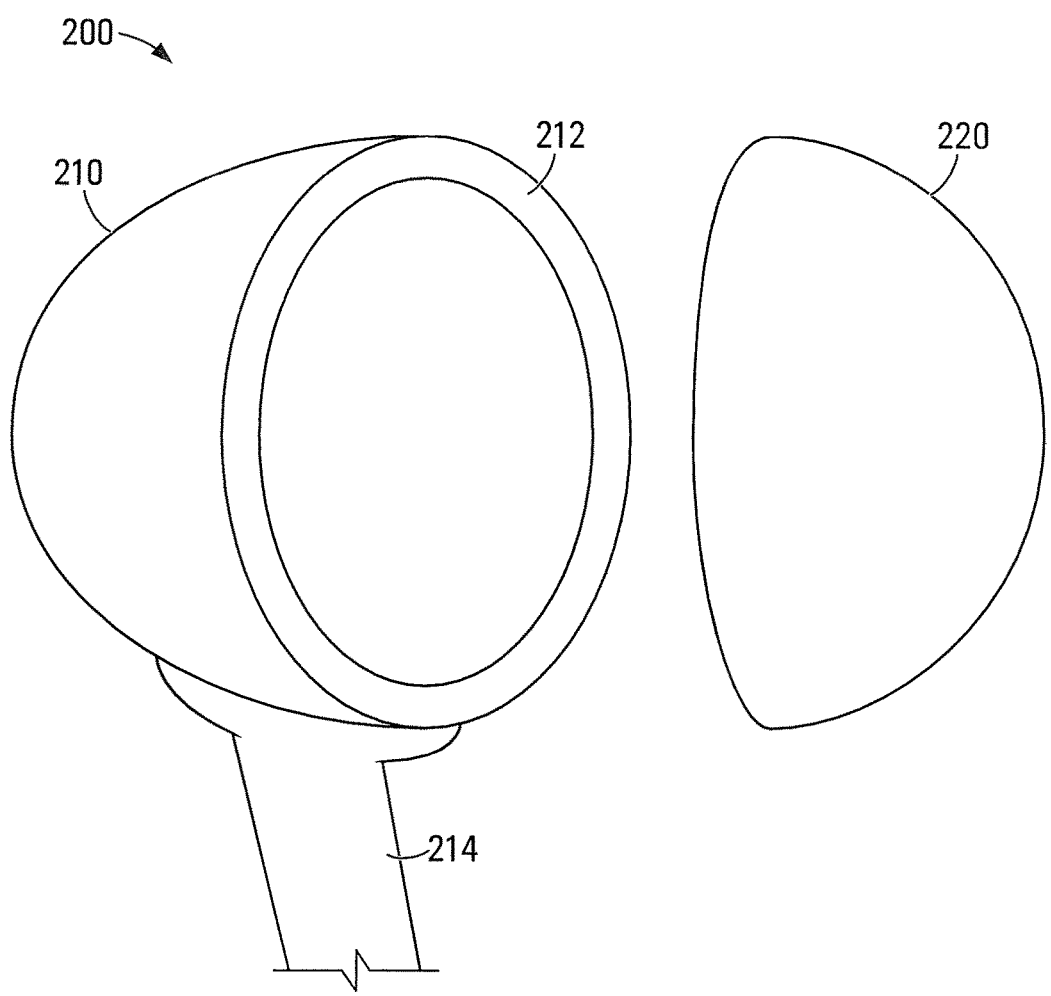
FIG. 4 shows a second front perspective view of two non-limiting sub-components, prior to the two sub-components being joined together to form an assembled component.

Shown in FIG. 4 is a non-limiting example of a hip implant 200 that is operative for replacing the rotator at the head of the femur. The hip implant 200, includes a femoral extension 214 that replaces part of the femur and secures the implant 200 to the bone. It should be understood that this non-limiting example focuses solely on the assembled hip implant 200, as the femoral extension 214 may be manufactured separately using a different process.

With reference to FIG. 4, it may be seen that the components of the hip implant 200 include a first sub-component 210 and a second sub-component 220. In this non-limiting embodiment, the first and second sub-components 210 and 220 each have an interior central hemispherical void so that the assembled hip implant 200 will have a hollow center.

For the purposes of this example, assume that the first and second sub-components 210 and 220 are made of different materials. For example, the first sub-component 210 may be formed from a cermet material powder (such as a ceramic/alumina alloy) in order to extend the operational life of the implant, while the second sub-component 220 may be formed from alumina material powder in order to further reduce the weight of the assembled hip implant 200.

At step 100, a feedstock is formulated for the first and second sub-components 210 and 220. The type of powder, type of binder and powder-to-binder ratio may be determined in a variety of ways. For example, it may be determined based on the empirical knowledge of a person skilled in the art depending on the desired specifications for the hip implant 200. Alternatively, a software application may be used to determine the feedstock formulations for these sub-components based on the desired specifications for the hip implant, a database comprising known feedstock formulations and experimental data related to their use.

Because the first and second sub-components 210 and 220 are to be joined, the size of particles in the material powder of their respective feedstocks may be adjusted in order to ensure that the first and second sub-components 210 and 220 begin to melt at approximately the same temperature during the sintering step and that the shrinkage rate of these sub-components will also be approximately the same. As mentioned above, this will help to avoid delamination of the assembled hip implant 200 along its mating surfaces during debinding and sintering. In order to do so, the particle size of the material powders used in the respective feedstocks may be adjusted. For example, the particle size of the material powder used in the feedstock for the first sub-component 210 may be reduced to cause this sub-component to melt at a lower temperature than if the base material had a larger particle size. The size of the particles of the base materials may be selected such that the first and second sub-components begin to melt at approximately the same temperature, and at approximately the same weight.

At the same time, a single binder formulation may be chosen for the feedstock of both sub-components, in order to allow the assembled hip implant 200 to be co-debound using a single debinding technique. For example, the binder used for the feedstock of both sub-components may be a solid form of PEG in order to allow the joined sub-components 210 and 220 to be co-debound using a water debinding technique.

Once the formulation for the feedstock of each of the first and second sub-components 210 and 220 has been determined, the feedstock may be produced and stored until needed. In accordance with a non-limiting example, it is possible that the one or more feedstocks are stored within sealed containers that may be safely transferred between locations in the same production facility or transported to a different production facility altogether.

At step 110, molds for each hemispherical sub-component are developed and prepared. This may be done based on computer-assisted design (CAD) files for the hip implant 200 and its constituent sub-components (i.e., the first sub-component 210 and the second sub-component 220). The mold materials may be chosen based on the size of the expected production run for the implant 200 and the expected rheological properties of the feedstocks for the sub-components 210 and 220, among other parameters.

During this step, reference features and mating surfaces for the sub-components may also be built into the molds.

At step 120, the feedstocks for the respective sub-components are injected into their respective molds, in order to form green parts for the first sub-component 210 and for the second sub-component 220. In order to inject the feedstocks into the molds, the feedstocks may be heated and mixed within a batch mixer until a homogenous mixture is produced. The heated feedstock is then injected to its mold for a specified time period (e.g., 30 seconds) at a specified pressure and temperature needed for the feedstock to conform to the shape of the mold. At the end of this period, the mold is opened and the green part for the sub-component is removed. In accordance with the present example, this step is performed in order to produce other first and second sub-components 210 and 220.

At step 130, the green parts for the first and second sub-components 210 and 220 are removed from the molds and are allowed to undergo a resting period to remove any residual stresses. During this step, each sub-component is transferred from the mold to a rest area, wherein it is allowed to rest for a period of time known to be sufficient to relieve residual stresses, which may be known from prior experience with similar components.

At step 140, the respective mating surfaces of the first and second sub-components 210 and 220 are prepared before they are joined to form the assembled hip implant 200. During this step, each pair of green parts for the first and second sub-components 210 and 220 may be inspected and treated in order to remove any flashing that might have accumulated on mating surfaces, which could prevent the sub-components from being joined together properly.

In addition, the mating surfaces may be treated in order to apply a bonding agent thereto. A non-limiting example of a bonding agent that could be used to help join the first and second sub-components 210 and 220 is a liquid form of PEG with a low molecular weight. This compound could be used as a bonding agent since the attraction between the high molecular weight PEG in the binder and the low molecular weight PEG in the bonding agent would hold the two sub-components 210 and 220 together, at least temporarily.

In addition, the use of soluble PEG as the bonding agent would allow the joined first and second sub-components 210 and 220 to be co-debound using a single application of the water debinding technique, which simplifies the debinding process for the assembled implant 200. In accordance with a non-limiting example, alumina powder may be added to the bonding agent. This extra alumina powder added to the bonding agent may strengthen the bond along the mating surfaces between the cermet-based first sub-component 210 (which is composed of a ceramic-alumina cermet material) and the alumina-based second sub-component 220 during sintering.

Figure 5:
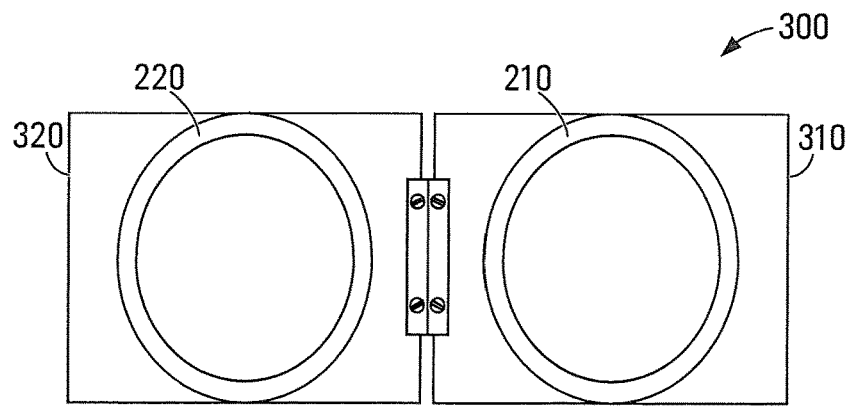
FIG. 5 shows a top plan view of a jig according to a non-limiting example, that may be used in order to place two sub-components into contact with each other.

At step 150, the first and second sub-components are joined together to form the assembled implant 200. FIG. 5 shows the mating surfaces along which the two sub-components 210 and 220 will be joined; namely mating surface 212 for the first sub-component 210 and mating surface 222 for the second sub-component 220. These mating surfaces 212 and 222 form a small rim along the interior circumference of each sub-component that surrounds an interior void.

The first and second sub-components may be joined together manually by placing their two mating surfaces 212 and 222 in contact with each other. The bonding material applied to the mating surfaces 212 and 222 should be sufficient to hold the two sub-components together at least temporarily, such that the co-debinding operation may be started on the assembled implant 200.

Figure 6:
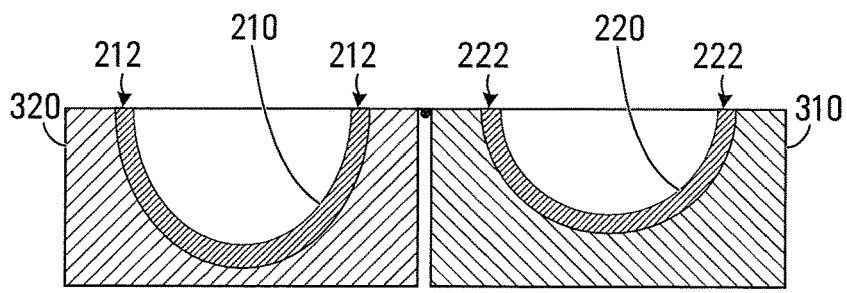
FIG. 6 shows a front cross-sectional view of the jig illustrated in FIG. 5 in an open position.

Alternatively, a jig may be used in order to hold the assembled sub-components together prior to, and possibly during, the co-debinding and sintering operations. Shown in FIG. 5 is a jig 300 that is constructed to allow more precise assembly of the hip implant 200 than could be achieved manually. FIGS. 5 and 6 show the construction of the jig 300, which is comprised of two opposed sections 310 and 320 that are hinged together along a common side so that the jig 300 may be folded open or closed like a book. The interior of each section contains a sized cavity made from a solid material (such as plastic) into which is set the green part for each to the two sub-components 210 or 220. The "fit" between a prospective sub-component and the jig cavity will make it obvious whether the correct sub-component has been inserted, and if so, whether it has been oriented correctly within the jig 300.

FIG. 6 illustrates the proper placement of the first and second sub-components 210 and 220 within the jig 300. This figure shows that the first sub-component 210 would not fit properly within the mold cavity within the section 320 that is designed for the second sub-component 220 and vice-versa. When the correct sub-component is inserted properly within its corresponding jig cavity its respective mating surface is generally flush with top of the cavity.

Next, the suspension containing the bonding agent and extra alumina powder is then carefully applied using a brush or similar applicator to the mating surfaces of the green parts to be joined. In this case, this suspension is applied to the mating surface 212 for the green part of the first sub-component 210 and to the mating surface 222 for the green part of the second sub-component 220 in order that such surfaces be coated with a miscible solution from the bonding agent, as well as with particles of the extra alumina powder.

Figure 7:
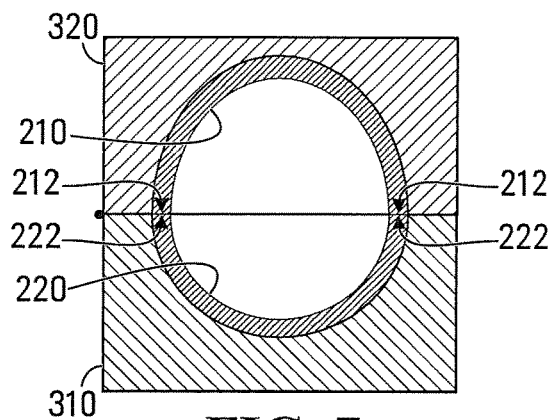
FIG. 7 shows a front cross-sectional view of the jig illustrated in FIG. 5 in a closed position.

At step 150, the jig 300 is slowly closed to bring the mating surfaces of the first and the second sub-components 220 together to form the assembled hip implant 200. FIG. 7 shows the position of the sub-components 210 and 220 when the jig 300 is closed. In this position, the coated mating surfaces 212 and 222 are brought into physical contact, thus allowing the bonding agent to join the hemispheres 210 and 220 (at least temporarily) and form the assembled hip implant 200.

When joined together, the two sub-components form a void within the interior of the assembled implant 200. The assembled implant 200 has a hollow center as a result, which helps to decrease its weight further.

At step 160, the joined green parts for the first sub-component 210 and second sub-component 220 are co-debound, such that the binder is removed while the two sub-components are in contact with each other. In accordance with this non-limiting example, the sub-components are co-debound using water debinding in order to remove the binder and bonding agent. During this step, the assembled hip implant 200 is immersed within a body of distilled water for a set period of time so that the soluble PEG in the binder and bonding agent may be extracted from the joined green parts for the hemispheres 210 and 220. Once co-debinding is completed, the assembled hip implant 200 is composed of its base materials, namely cermet particles within the first sub-component 210 and alumina particles within the second sub-component 220, with additional particles from the extra alumina powder deposited along the interface between them.

At step 170, the debound assembled hip implant 200 is then sintered such that the powder particles melt and bond together. This increases the density of the component as the powder particles melt and fill in the pores left by the binder.

A sintering profile is used to control the temperature of the furnace at a preset ramp rate up to a given sintering temperature that is sufficient to sinter the assembled hip implant 200. This sintering temperature may be determined on the basis of a variety of different factors, such as the melting point of the materials and the desired rate at which the melting and sintering occurs. In accordance with a non-limiting embodiment, the sintering temperature is maintained over a specified time period during which the particles of cermet and alumina in each sub-component partially melt and bond together, filling the voids left by the extracted binder. During this period, the density of the assembled hip implant 200 increases and its porosity decreases as the particles in each sub-component bond with each other. At the same time, material particles along the interface of the first sub-component 210 and second sub-component 220 (namely, those along the mating surfaces 212 and 222 in physical contact) partially melt and bond with particles of the other sub-component, thus creating a joint between the sub-components 210 and 220. In addition, the particles from the extra alumina powder that had been deposited with the bonding agent melt and bonds with particles in both of the sub-components 210 and 220, thus reinforcing the joint between them and strengthening the assembled hip implant 200 further.

During the method described above, it is desirable that the sub-components of the assembled hip implant 200 shrink in size at approximately the same rate. By having the sub-components of the assembled implant 200 shrink in substantially the same way, the joint between these sub-components is protected against delamination and separation.

Although a hip-rotator has been described above, it should be appreciated that this co-processing method for joining sub-components may be used in order to make a variety of different pieces of medical equipment, including surgical tools, surgical guides, implants, etc.

Figure 8:
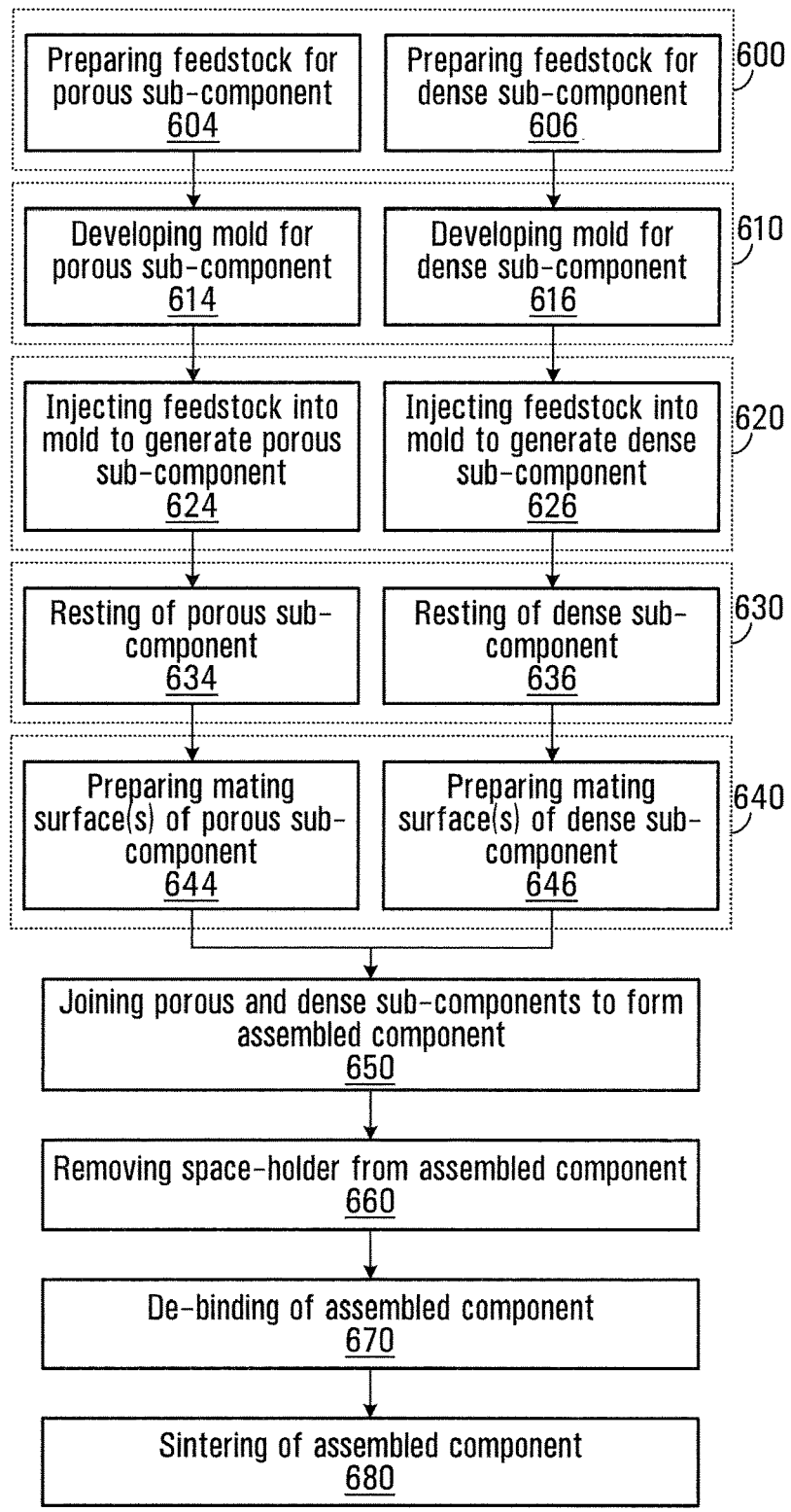
FIG. 8 shows a flow diagram of a second non-limiting co-processing method in accordance with a specific example of implementation of the present invention.

Method 2: A Co-Processing Method for Joining a Porous Component with a Denser Component FIG. 8 shows a non-limiting flow diagram of a method in accordance with a second example of implementation of the present invention. This method involves performing a co-processing operation in order to assemble together a porous sub-component and a more dense sub-component. As used for the sake of this method, the term "porous" refers to a sub-component containing void spaces within its formed structure, which may be intentionally created using a process described below. It should be appreciated that all of the sub components will contain porosities, given that they are formed via a MIM manufacturing process. However, the sub-component that is being referred to herein as "porous" will include void spaces created as a result of a foaming operation or as a result of including space holders within the feedstock.

As shown, this method involves preparing a feedstock for each of the sub-components that are to be joined together, injecting the feedstock(s) into respective molds for producing "green" parts for each of the sub-components, joining the sub-components together to form an assembled component, removing the space-holder from the porous sub-component, performing co-debinding step for removing the binder from the assembled component and then sintering the assembled component to form the final assembled part. Further details for each of these steps will be described below.

Step 600

At step 600, a feedstock material is prepared for each of the sub-components that are to be joined together. In the non-limiting example shown, step 600 is represented by two boxes, 604 and 606, each representing the preparation of a feedstock for one of the respective sub-components.

Step 604 represents the preparation of the feedstock for the porous sub-component. The feedstock for the porous sub-component is formed from a material powder and a binder, as described above with respect to step 100 in FIG. 1. In addition, the feedstock for the porous sub-component includes an additional "space-holder" component that is included in order to create large porosities within the porous sub-component.

More specifically, the purpose of the space-holder is to produce void spaces within the sub-component. This is done by eventually removing the space-holder from the formed feedstock, which leaves voids within the formed shape. Therefore, the space-holder is typically a particulate whose size exceeds that of the material powder and/or binder in the feedstock. Non-limiting examples of types of space-holders that may be incorporated within the feedstock include salts (e.g., granules of table salt (NaCl)), polymeric materials (e.g., drops of wax or particles of polymers like PEG), and/or organic material particles, such as wood chips.

In accordance with a non-limiting embodiment, the space holders may have a diameter of greater than 100 microns.

Step 606 represents the preparation of the feedstock for the denser sub-component. The feedstock for this sub-component does not contain any space-holders such that the second sub-component will be denser than the porous component. In accordance with a non-limiting example, the feedstock for the denser sub-component is a wax-based feedstock with approximately 75% wax that has a melting point below 60 degrees C. Since details about the preparation of the feedstock for the denser sub-component have already been provided in the context of the previous method, further details about this step will not be provided here.

In accordance with a non-limiting example of implementation, the same feedstock with the same solid loading of powders is used for both the porous sub-component and the denser sub-component, with a difference being that the porous sub-component includes the space-holders.

Step 610

At step 610, molds for each of the individual sub-components are developed and prepared. The activities associated with steps 600 and 610 (namely, feedstock and mold preparation) are separated here for the sake of explanation. However, it is possible that step 610 occurs simultaneously with, or even precedes, step 600, and as such the flowchart presented for these two steps in FIG. 6 should not be construed as a limitation of this method.

In the non-limiting example shown in FIG. 8, step 610 is represented by two boxes, 614 and 616, each representing the development and preparation of a mold for one of the respective sub-components. As previously described, both molds may contain reference features (such as guide arrows, extrusions/notches or attachments for a jig) to assist the joining of the two sub-components to form the assembled component.

Since the processes and techniques for developing MIM-related molds are substantially the same as those presented with respect to the first method, and are also believed to be well known to persons of skill in the art, further explanation of this step will not be provided herein.

Step 620

At step 620, the feedstocks are injected into the molds that were prepared during step 610 to generate green parts for both sub-components. During this step, the feedstock for each of the at least two sub-components is injected into its respective mold so that the feedstock may assume the shape of the mold. In the embodiment shown in FIG. 8, this step is represented by two boxes, 624 and 626, each of which represents the injection of feedstock into a respective mold for one of the sub-components.

As before, a feedstock is injected into its respective mold at a specified temperature, pressure and injection rate, depending on the rheological characteristics of the feedstock, as well as any predetermined molding conditions.

For the denser sub-component, a low pressure injection molding process may be used to inject the feedstock into its mold, which involves injecting the feedstock into the mold at a pressure of less than 80 psi and at a temperature of below 80 degrees C.

Generally, the molding conditions for porous sub-components are similar to those for denser sub-components, especially where the feedstock for both components contains a polymeric wax binder. However, it is also possible that molding conditions to produce green parts for porous sub-components may be performed at even lower injection pressures, such as pressures of 80 psi or less.

Since the process for injecting feedstock into a mold and generating green parts in a MIM manufacturing process is similar to that described previously in the context of the first method, no further explanation of this step will be provided.
Step 630

At step 630, the green parts for the first and second sub-components are removed from their respective molds and then undergo a resting period. In FIG. 8, this step is represented by two boxes, 634 and 636, each of which represents the resting period for one of the green parts formed for each of the sub-components. The resting period allows the formed feedstock within the green parts to settle into their new molded shapes in order to eliminate any residual stresses that might otherwise cause delamination or separation of the two components during the debinding and sintering phases.

Since it is believed that a person of skill in the art will be able to determine an appropriate resting period for the green parts, further explanation of this step will not be provided herein.
Step 640

At step 640, the mating surfaces of the two sub-components are prepared for assembly. In the embodiment shown in FIG. 8, this step is represented by two boxes, 644 and 646, each of which represents the preparation of one of the respective sub-components to be joined.

As before, the preparation of the mating surfaces may involve a plurality of different operations, including the removal of any "flashing" from the surfaces of the sub-components (and especially their mating surfaces), as well as the application of a bonding agent to their mating surfaces to help the sub-components remain together once joined.

It should be noted that the formulation of a bonding agent for a porous sub-component remains related to the composition of its feedstock, and in particular to the binder(s) used in this feedstock.

In the description of the first method, it was mentioned that the bonding agent for the sub-components may be in a liquid form (such as Oleic acid) to simplify its application to the mating surfaces. While a liquid bonding agent may be used for this method as well, the selected bonding agent may also include a certain amount of additional material powder. In this way, any localized removal of space-holders that may result from the application of the bonding agent to the mating surface(s) of the porous sub-component may be replaced with material powder to strengthen the physical bond between the joined sub-components.

In the non-limiting example of the method presented in FIG. 6, the generation of the green parts for both the porous sub-component and the denser sub-component use standard MIM production methods. However, other production methods could also be used to produce these green parts without departing from the scope of the invention. For example, the green part generated for the porous and/or denser sub-component(s) could be created using a machine press that compacts the feedstock into a molded shape, rather than injecting it into a mold. In addition, the porous sub-component may be generated from a feedstock that is "foamed", meaning it is already porous when in its green state.
Step 650

At step 650, the mating surfaces of the first and second sub-components are placed into physical contact with each other in order to form the assembled component. When joining these sub-components, the alignment, position and orientation of their mating surfaces may be determined based on their geometry, or based on any reference features, such as guide arrows or similar markings. Alternatively, sub-components may be joined where the mating surfaces may be an integral part of the reference features, (e.g., a groove and projection), and/or use a jig or tool where a more precise orientation and alignment of the sub-components is deemed necessary.

Although step 650 is presented as a single step, it may be possible that the formation of the assembled component may require multiple iterations of the orientation, alignment and joining of a number of porous and denser sub-components that are needed to form the assembled component.
Step 660

At step 660, the space-holders are removed from the porous sub-component of the assembled component. For example a solvent removing process or a thermal removing process may be used depending on the type of space-holder that was added to the feedstock of the porous sub-component. For example, soluble space-holders (such as salt granules) may be removed from an assembled component via a solvent removing process, such as immersion in water. As the space-holders dissolve within the water, they leave behind void spaces that render that sub-component porous.

It should be appreciated that the space holders leave behind void spaces that are larger than the porosities that are left behind as a result of the debinding process. For example, the void spaces created by the removal of the space holders may have a diameter of greater than 100 microns, whereas the porosities created by the removal of the binder, generally leave porosities having a diameter of less than 10 microns, and more particularly between 2-5 microns.

It should be appreciated that any method of removing the space holders may be used, such as via solvents, thermal treatments or any other method known in the art.

Although the step of removing the space-holders is shown in FIG. 8 as occurring after the porous sub-component and the denser sub-component have been joined together, the removal of the space-holder could also have been done prior to joining the sub-components together. For example, the space-holders could have been removed following step 630 of the method.
Step 670

At step 670, a co-debinding operation is performed on the two sub-components that have been joined together to form the assembled component. During this step, the binder (and in some cases the bonding agent), are removed from the joined sub-components, leaving the material powder within the form of the assembled component.

It is worth noting that the void spaces created by the removal of space-holders during the previous step may provide additional exit routes for the binder(s). This may help reduce the time and resources required for co-debinding, as well as help reduce or prevent stresses from building in the various sub-components that could potentially cause delamination and/or separation of the assembled component. In addition, the debinding step may further remove any residual space-holders that remained after the step 660.

Since the process for co-debinding the assembled component is similar to that described previously with respect to method 1, further explanation of this step is unnecessary.
Step 680

At step 680, the assembled component is sintered in an oven or furnace at a temperature high enough to cause the particles of material powder in the joined sub-components to at least partially melt and bond together, thus increasing the density of the assembled component.

Although the porosity of the assembled component (including the porous sub-components therein) generally decreases during the sintering phase, it is unlikely that the void spaces created by the space-holders in the porous sub-components are reduced significantly. As a result, these void spaces are likely to remain open, even as the general porosity of the assembled component decreases.

It will be noted that in the non-limiting example of the method illustrated by FIG. 8, space-holder removal (step 660), debinding (step 670) and sintering (step 680) are presented as independent steps. In some cases, however, it may be possible to combine two or more of these three steps, especially where the space-holder and binder are closely related. In certain circumstances the space-holder removal and debinding may take place at the same time. This is the case when the space-holder and binder may both be removed by either solvent debinding or thermal debinding. For example, the porous sub-component may include a type of space-holder that changes from a solid to a gaseous state when heated. If the preferred debinding method for the assembled component is thermal debinding, it may be possible to remove the space-holders from the porous sub-component at the same time that the assembled component is being debound. Once the space-holder removal and debinding have taken place, the sintering process may then be performed. In some cases, the thermal debinding may also act to sinter the components, such that all three steps are combined into a single process.

Furthermore, in an alternative embodiment, the porous sub-component may be both debound and sintered prior to being joined to the second sub-component.

Since the techniques used to develop sintering profiles and sinter MIM-produced components have been discussed in the context of prior methods, and are also assumed to be well known in the art, further explanation of this step need not be provided herein.

The method described above for producing an assembled component that has both a porous portion and a more dense portion is suitable for producing medical implants. For many implants, it is advantageous to have a porous end that is able to promote osteo-integration with the patient's bone, and a more dense portion that provides structural rigidity and strength to the implant. Moreover, in the case where the material of the dense portion integrates into the porosities of the porous portion, the end result is a graded component that transitions more gradually from a porous component to a more dense component.

Figure 9:
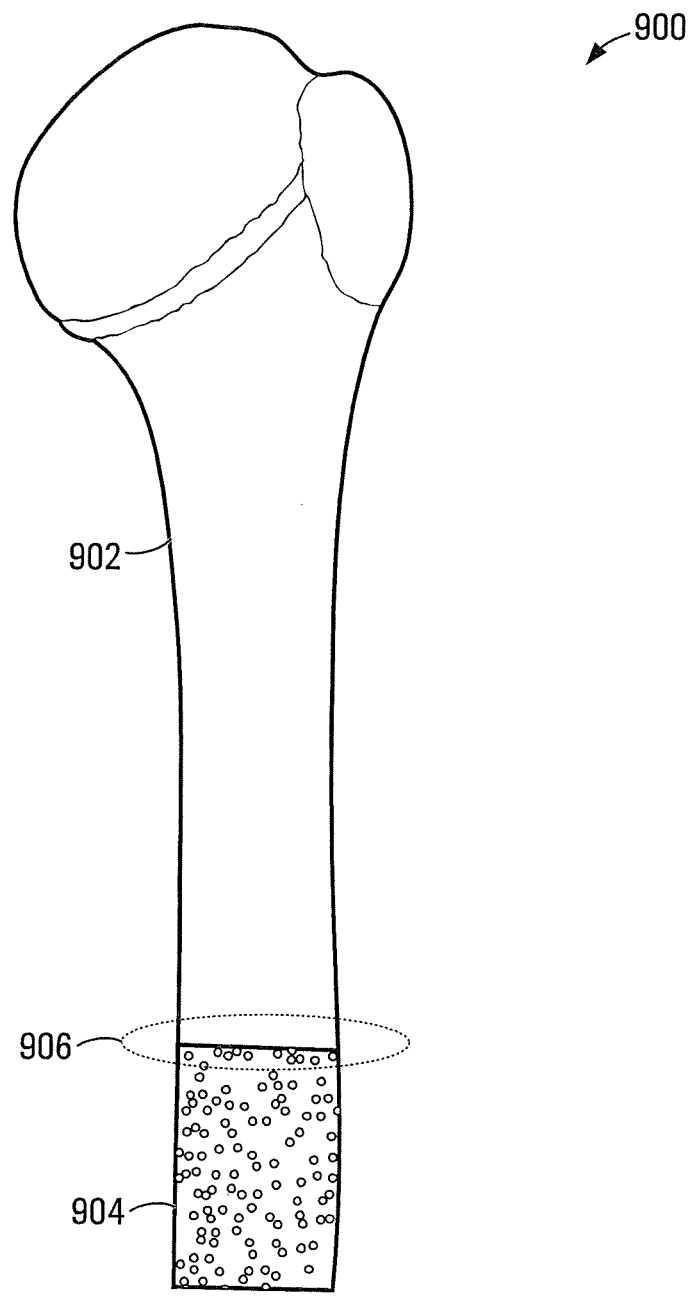
FIG. 9 shows a non-limiting example of a medical component formed via the co-processing method of FIG. 8.

Shown in FIG. 9 is a non-limiting example of a component formed according to method 2 described above. In the non-limiting example shown, the medical component is a bone implant 900, that includes a first relatively dense sub-component 902 joined to a second porous sub-component 904, such that the assembled component provides a gradation of density along a longitudinal axis of the assembled component.

Although the medical component shown in FIG. 9 is a bone implant 900, it should be appreciated that the medical component may be a surgical implant, such as a hip implant, or other orthopaedic implant, or could also be a surgical tool or a cutting guide, among other possibilities.

The first sub-component 902 is formed from a first metal material via a metal injection molding process. As such, due to the removal of the binder material from the first sub-component, once it has been sintered, the spaces where the binder once was leaves small porosities. As such, the first sub-component will be less dense than it would be if it was made from the same metal material in a pure block form. In accordance with a non-limiting embodiment, the first sub-component 902 has a density of less than 99% of a theoretical possible density, which is the density of the same metal material in its pure form. The manner of calculating density is described in detail above.

The second sub-component 904 is formed from a second metal material also via a metal injection molding process. However, the feedstock that is used to form the second sub-component 904 further comprises space-holders. As such, when the space-holders have been removed, void spaces are left within the second sub-component. Furthermore, when the binder material has been removed, small porosities are also left behind. Once the second sub-component 904 has been sintered (which is performed at the same time as the sintering of the first sub-component 902), both void spaces from the removal of the space holders and porosities from the removal of the binder are left within the second sub-component 904. As such, the second sub-component 904 will be less dense than the first sub-component 902. In general, the second sub-component will have a density of less than 99% of a theoretical possible density, which is the density of the same metal material in its pure state. And more specifically, the second sub-component will have a density of less than 97% of the theoretical possible density.

The first sub-component 902 and the second sub-component 904 can be made of the same metal material, or different metal materials, depending on the desired performance characteristics of the finished component. Some non-limiting examples of materials that can be used for the first sub-component 902 and the second sub-component 904 may include stainless steel alloys, cobalt-chrome alloys, titanium, titanium alloys, alumina ceramics and cermets, as well as zirconia ceramics and cermets, among other possibilities.

In the case of the bone implant 900 shown in FIG. 9, the first sub-component 902 is formed via a MIM process in order to be relatively dense, so as to provide strength characteristics to the finished bone implant 900. Whereas, the second sub-component 904 is formed via a MIM process in order to have void spaces that facilitate osteo-integration with human bone. As such, the space holders that are used within the feedstock that forms the second sub-component 904 are chosen so that the portion of the bone implant 900 that is formed from the second sub-component provides void spaces that match the porosity of a given human bone. For example, the void spaces can be formed to have substantially the same volume as the porosities in the given human bone. This will help to facilitate osteo-integration of the human bone with the bone implant 900.

Once the first sub-component 902 and the second sub-component 904 have been joined together, the finished bone implant 900 provides a gradation in density along its longitudinal axis. More specifically, from one end of the bone implant 900 to the other, the bone implant 900 provides a gradation in density that goes from a relatively dense end of the bone implant 900 to a less dense end of the bone implant 900. It should be appreciated that for medical components having different shapes, the gradation in density may occur along a transversal axis instead of a longitudinal axis.

Although only two sub-components 902 and 904 have been shown in FIG. 9, it should be appreciated that multiple different sub-components could be used in order to form a medical component according to the present invention. In the case where multiple sub-components are used, it is possible that each sub-component may have a different density, such that when joined together to form the finished component, the gradation in density provided by the finished component occurs more gradually along one of the longitudinal axis and the transversal axis.

With further reference to FIG. 9, the first sub-component 902 and the second sub-component 904 are joined together at a region of interface 906. The region of interface 906 is located in the vicinity of where the mating surfaces of two sub-components 902 and 904 are joined. By performing co-debinding and co-sintering of the two sub-components 902 and 904, the region of interface 906 between the first sub-component 902 and the second sub-component 904 is substantially seamless. Although in the case where the densities and/or amount of void spaces between the two sub-components differ, it is possible that there will be somewhat of a visible seam between the two sub-components. However, to the touch, the region of interface will be substantially seamless.

Furthermore, the bond strength that is created between first sub-component 902 and the second sub component 904 is substantially constant throughout the contact area of the mating surfaces.

Method 3: An Over-Molding Co-Processing Method

Figure 10:
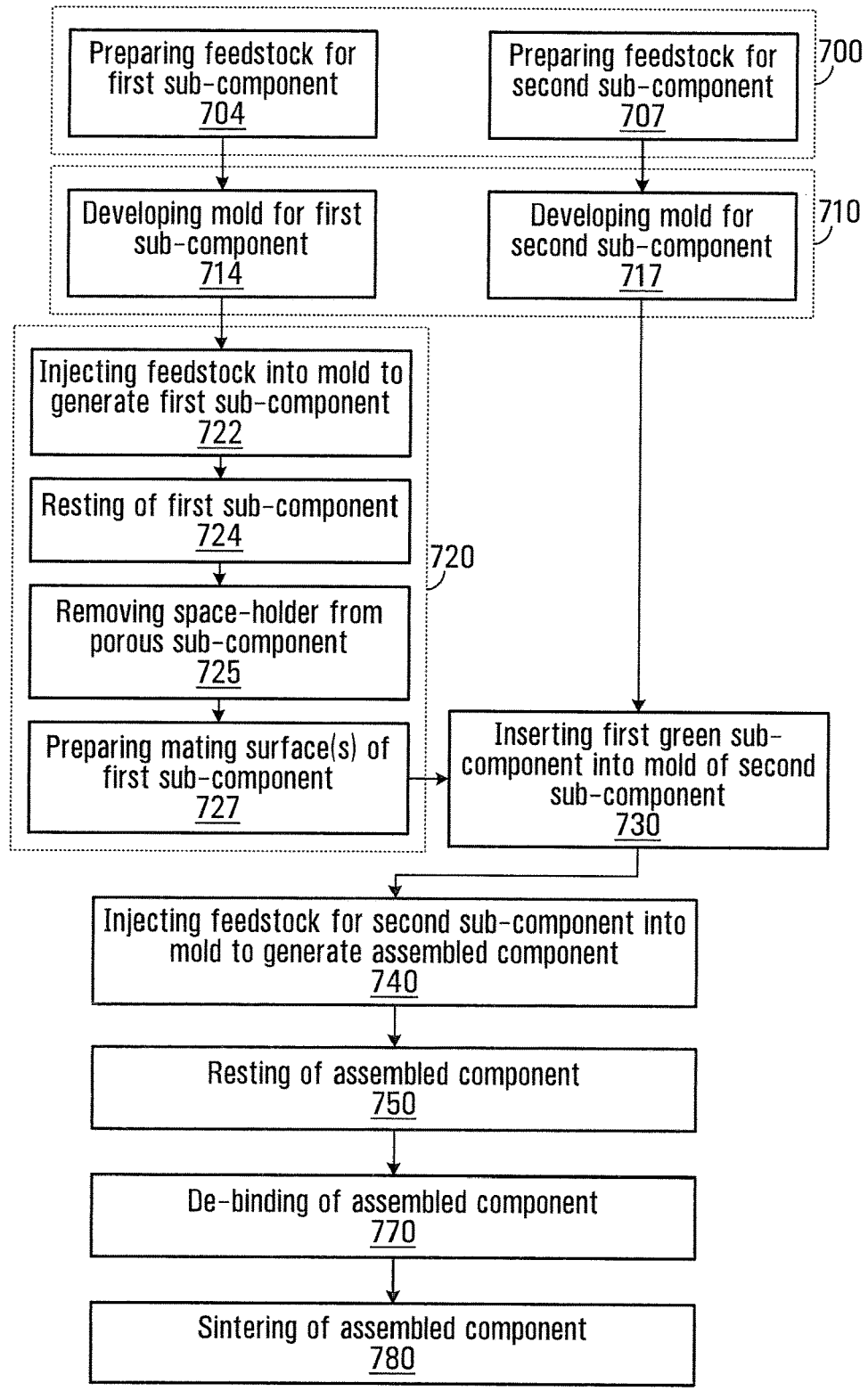
FIG. 10 shows a flow diagram of a third non-limiting co-processing method in accordance with a specific example of implementation of the present invention.

FIG. 10 shows a non-limiting flow diagram of a method in accordance with a third example of implementation of the present invention. An assembled component that is created through this method is generated by "overmolding" one sub-component over another. As used here, the term "overmolding" refers to a method of attaching two sub-components by partially or wholly molding a second sub-component over a first sub-component, which for the purposes of this description will be a porous sub-component.

As used herein, the term "porous" refers to a material containing void space(s) within its formed structure, which may be intentionally created using a process described below. It should be appreciated that all of the sub components described herein will contain porosities, given that they are formed via a MIM manufacturing process. However, the sub-component that is being referred to herein as "porous" will include void spaces created as a result of a foaming operation, or as a result of including space holders within the feedstock.

As shown in FIG. 10, the method of overmolding involves preparing a feedstock for the first and second sub-components, developing molds for these two sub-components, generating the green part for the first sub-component to be overmolded, inserting the green part within the mold of the second sub-component, joining the two sub-components together by overmolding the second sub-component over the first sub-component, performing co-debinding in order to remove the binder from the assembled component while the components are in physical communication with each other, and then sintering the assembled component to form the final part. Further details for each of these steps will be described below.

It should be understood that the description and the example provided below refer to an assembled component that is formed by joining two (2) sub-components together through overmolding. In addition, the description refers to a porous sub-component that is joined with a denser sub-component. It should be appreciated that the present method is not limited to joining only two sub-components together, nor is it limited to assembling a porous sub-component with a denser sub-component. Indeed, this method may be used to form an assembled component that has any number of porous and/or denser sub-components joined together.

Step 700

At step 700 of the method shown in FIG. 10, a feedstock material is prepared for each of the sub-components that are to be joined together. In the non-limiting example shown in this figure, step 700 is represented by two boxes, 704 and 706, each representing the preparation of a feedstock for one of the respective sub-components.

Step 704 represents the preparation of the feedstock for the first sub-component, which for the purposes of this example, will be a porous sub-component. The feedstock for this sub-component contains a material powder and binder as described above in reference to step 100 in FIG. 1. In addition, the feedstock for the porous sub-component includes an additional so-called "space-holder" component that is included in order to create void spaces within the porous sub-component.

The purpose of the space-holders is to produce void spaces within the sub-component, which is done by eventually removing the space-holder from the formed feedstock, which leaves void spaces within the formed shape. Therefore, the space-holder is typically a particulate whose size exceeds that of the material powder and/or binder in the feedstock. Non-limiting examples of types of space-holders that may be incorporated within the feedstock include salts (e.g., granules of table salt (NaCl)), polymeric materials (e.g., drops of wax or particles of polymers like PEG), and/or organic material particles, such as wood chips.

It should be appreciated that the space holders leave behind void spaces that are larger than the porosities that are left behind as a result of the debinding process. For example, the void spaces created by the removal of the space holders may provide a void spaces having a diameter of greater than 100 microns, whereas the porosities created by the removal of the binder, generally leave porosities having a diameter of less than 10 microns, and more particularly between 2-5 microns.

The type of space-holder selected for the feedstock may be chosen depending on certain desired characteristics for the sub-component, such as the desired size of voids to be generated by the space-holder, the desired porosity of the sub-component and the intended method of removing the space-holder, which may be related to the overall debinding method for the assembled component.

Typically, the space-holder component is removed from the formed sub-component prior to the debinding and/or sintering phases. Therefore, the addition of the space-holder to the feedstock of the porous sub-component is unlikely to have an effect on its shrinkage behaviour during the sintering of the assembled component. As a result, the adjustment techniques (such as the adjustment of material powder particle size) previously introduced to maintain generally constant shrinkage behaviour during sintering may be applied equally to the denser sub-component and the porous sub-component.

The process for selecting a space-holder for the porous sub-component may be done in a variety of ways that will be known to a person skilled in the art, and as such will not be explained in further detail herein. In some cases, this selection process may be performed with the help of a software application that analyzes the specification and desired characteristics for a part or tool and makes recommendations as to the space-holder (as well as the binder and/or material powder) that would best meet these specifications and characteristics.

Step 706 represents the preparation of the feedstock for the second sub-component, which for the purposes of this example, will be a denser sub-component that does not include the space-holders. In accordance with a non-limiting example, the feedstock for the denser sub-component is a wax-based feedstock with at least 75% wax that has a melting point below 60 degrees C. The process for preparing the feedstock will be substantially the same as the process described above with respect to Step 100 of FIG. 1. In accordance with a non-limiting embodiment, the powder material of the second feedstock is titanium, or a titanium blend.

In accordance with a non-limiting example of implementation, the same feedstock with the same solid loading of powders is used for both the porous sub-component and the denser sub-component, with a difference being that the porous sub-component includes the space-holders.

Step 710

At step 710, molds for each of the individual sub-components are developed and prepared. While FIG. 7 shows this step occurring after the preparation of the feedstock for the sub-components, it is possible that these two steps occur simultaneously or may be reversed. For example, it is possible that the molds are developed and prepared prior to the formulation of the one or more feedstocks. In some embodiments, the rheological properties of the feedstock and the characteristics of the mold are considered together in order to determine optimal molding conditions for a particular sub-component.

In the non-limiting example shown in FIG. 7, step 710 is represented by two boxes, 714 and 716, each of which represents the development and preparation of a mold for one of the respective sub-components. Although the materials and preparation methods for molds are generally similar to those introduced in the previous method (namely, with respect to step 110 in FIG. 1), there are certain differences due to the overmolding process that is used to join the sub-components together, which are described below.

For example, the mold for the first sub-component (i.e., the component that is to be overmolded), may include reference features that indicate how the first sub-component should be oriented, positioned and/or brought into physical contact with the mold for the second sub-component. In addition, reference features may also be used to indicate attachment points for ancillary attachment devices (such as pegs or stands) that may be used to keep the first sub-component properly oriented and/or positioned with the mold of the second sub-component.

Likewise, the mold for the second sub-component is likely to include reference features that indicate where and how the first sub-component (and any ancillary attachment devices) are to be oriented and/or positioned within it. For example, the mold used to generate the first sub-component may include alphanumeric characters and a reference arrow that are also included within the mold of the second sub-component. Through these reference features, the green part generated for the first sub-component may be properly aligned and positioned within the mold of the second sub-component so that it may be overmolded by the feedstock of the second sub-component.

The overmolding process may also result in an increase in the size of each mold, especially that of the second-sub-component. Because the second sub-component incorporates the first sub-component, the dimensions of this mold may need to increase accordingly to accommodate both the volume of the first sub-component and the amount of feedstock needed to overmold this sub-component.

Furthermore, the incorporation of a porous sub-component within the assembled component may also have certain impacts on the overall size of the molds. In particular, the feedstock of a porous sub-component contains a space-holder, which may require a change in the amount of feedstock that needs to be injected to produce this part. Moreover, the feedstock intended to produce a porous sub-component is typically injected into the mold at a lower pressure. For example, the feedstock for the porous sub-component may be injected into the mold at a pressure of less than 80 psi. As a result, the dimensions and/or materials selected for this mold may be different than would otherwise be the case.

It is likely that the process of generating molds may be performed with the help of a software application that analyzes the specifications, design and/or CAD files of each of the two sub-components and makes recommendations and/or adjustments to the mold design that would best accommodate such differences.

Step 720

At step 720, the first sub-component, which for the purposes of this example is the porous sub-component, is formed.

In the non-limiting embodiment shown in FIG. 10, the porous sub-component is produced using MIM production techniques. The activities involved with the production of the green part for this porous sub-component are represented by the boxes 722, 724 and 726, which respectively represent the injection of the MIM-related feedstock, resting of the green part, removing the space-holder and optionally, preparation of the mating surface.

Steps 722, 724 and 726 are similar to steps 120, 130 and 140 of FIG. 1, and as such will not be described in more detail herein. However, with regards to step 722, in general, the porous sub-component is injected into the mold via low pressure injection molding, such that it is injected at a pressure of less than 80 psi and at a temperature of less than 80 degrees C. However, in the case where the porous feedstock contains the same wax as is used in the feedstock for the denser component, it is possible that the porous sub-component may be injected at higher pressures.

With regards to step 725, the space-holder is removed so as to create the porous portion of the assembled component. The procedure for removing the space-holder from the assembled component depends on the type of space-holder incorporated into the feedstock. For example, in the case where granules of salt are used as the space-holder, a solvent removal procedure may be performed. More specifically, since salt is water-soluble, the component may be immersed in water to dissolve the salt granules and cause the component to become porous.

Alternatively, if the space-holder includes wax particles or wood chips, a suitable removal process is performed that will remove such space-holders from the green part, thus leaving a porous green part. It should be appreciated that in an alternative embodiment, the space-holder may be removed at a later stage when the feedstock of the second sub-component has been overmolded over the first sub-component.

It is worth noting that although the non-limiting example represented by step 720 results in the production of a green part through standard MIM production techniques, this need not be the case. For example, it is possible that the first sub-component generated as a result of step 720 may not be a green part, but a sub-component that has already been debound and sintered.

Alternatively, the green part provided at step 720 may have been produced using production techniques other than MIM. For example, the green part may have been created using a machine press to compress the feedstock into a mold rather than having it injected into a mold. If the green part is porous, it may also be possible that the feedstock from which this part is created is already "foamed", meaning it is already porous in its green state. Other methods of producing and/or providing the green part at this step would also fall within the scope of the invention.
Step 730

At step 730, the first sub-component, which in this case is the porous sub-component, is inserted into the mold of the second sub-component so that it may be overmolded by the feedstock of the second sub-component.

As described at step 710, it is possible that certain reference features may be used to assist the orientation and positioning of the first sub-component within the mold of the second sub-component. For example, certain guide markings or arrows in the mold of the second sub-component may correspond to similar features molded into the formed feedstock of the first sub-component, which show its proper orientation and position.

The first sub-component may be positioned within the mold of the second sub-component such that a portion of the first sub-component will be overmolded. Or alternatively, in certain applications, the first sub-component may be intended to be completely surrounded and/or enclosed by the feedstock of the second sub-component. In such cases, it is likely that certain attachment or positioning devices (such as pegs or stands that support the sub-component) may need to be used to maintain the position of the first sub-component during the injection of the feedstock of the second sub-component. During this step, these devices may be positioned within the mold of the second sub-component.

For example, a porous first sub-component may be positioned to act as a central core of the assembled component in order to reduce its weight. In this case, the porous first sub-component may be placed on pegs or stands during this step that will subsequently allow the feedstock of the second sub-component to completely surround and enclose the first sub-component.
Step 740

At step 740, the feedstock for the second sub-component is injected into the mold containing the first sub-component.

As the feedstock of the second sub-component is injected into its mold, it encounters the exterior surface of the first sub-component within the mold. In accordance with a first non-limiting example, the feedstock of the second component will be overmolded over a portion of the porous sub-component, thus partially surrounding the first sub-component and leaving some of the first sub-component exposed. For example, the feedstock of the second component may be overmolded over only an end portion of the porous sub-component, such that the assembled component will be a graded component that is porous at one end, and more dense at another end.

In the case where the space-holder is removed from the first sub-component prior to the overmolding, the feedstock of the second sub-component may infiltrate the porosities within the first sub-component, thus creating a good mating bond with the first sub-component. In the case where the feedstock of the second component moves into the porosities of the first sub-component, it is possible that step 726 of preparing the mating surfaces does not need to be performed.

Alternatively, the feedstock of the second sub-component may completely enclose the first sub-component.

Typically, the injection of the feedstock for a MIM component follows certain molding conditions that define the feedstock temperature, injection pressure and mold temperature, among others. Generally, the feedstock for the second sub-component is injected via a low pressure injection molding process, which involves injecting the feedstock into the mold at a pressure of less than 80 psi and at a temperature of below 80 degrees C. Injecting the feedstock of the second sub-component at lower pressure helps to prevent movement of the first sub-component that could cause unwanted shifts in the position and/or orientation of this sub-component within the resulting assembled component. Furthermore, overmolding the porous component (previously treated to remove space holder and reveal voids) when done at low pressure (ex: lower than 80 psi) may allow the formation of a resistant bond/interface since some of the overmolded feedstock may infiltrate the voids at the interface, but not excessively flow (due to low pressure and low temperature and associated rheology of the feedstock) to fill all or a considerable amount of the voids in the porous part and thus eliminate the voids.

At step 740 the attachment process occurs within the cavity of the mold for the second sub-component. As a result, this process prevents human interaction or contact with the sub-components during the joining process, which may advantageously reduce the ability of contaminants (such as organic bacteria or particulates of heavy metals) to enter the assembled component. For example, assembling medical or dental tools or components using this method could prevent potential organic and/or inorganic contaminants from being inadvertently transferred from the person assembling the tool or part.
Step 750

At step 750, the assembled component undergoes a resting period that is intended to remove residual stresses from the assembled component, and in particular, from the formed feedstock of the second sub-component, which has been molded over the first sub-component. This resting period allows the formed feedstock for both sub-components to settle so as to prevent unexpected deformations during the upcoming debinding and/or sintering phases.

The processes for determining the resting period for the assembled component in this method is similar to that which was previously described with respect to step 130 in FIG. 1.
Step 770

At step 770, a debinding operation is performed on the joined sub-components that form the assembled component.

In the case where the space-holder was not removed from the porous sub-component prior to the overmolding process, the space-holder may be removed prior to, or simultaneously with the debinding operation. For example, it may be possible to combine the processes for removing space-holders and the binding material. If both the space-holder in the porous sub-component and the binder for the assembled component are water soluble (e.g., table salt for the space-holder and PEG for the binder), both could be removed from the assembled component through immersion in water, such as using a water debinding technique.

In another non-limiting example, assume that both the space-holder and binder in the feedstock are reactive to heat, such as where wood chips are used as the space-holder for the porous sub-component and a polymer (such as wax or polypropylene) is used as a shared binder for all sub-components. In this case, the assembled component may be thermally debound, with the applied heat likely causing the particles of wood to incinerate as the binder is being removed. The removal of the wood chips results in void spaces being created within a portion of the assembled component intended to be porous.

In the case where the space-holder has been removed prior to the overmolding, step 770 is operative to simply remove the binder from the assembled component. Any appropriate debinding technique, such as thermal debinding or solvent debinding, may be used. This step is substantially similar to step 160 described previously with respect to FIG. 1, and as such will not be described here in further detail.

Step 780

At step 780, the assembled component is sintered in an oven or furnace. During this process, particles of the material powder(s) in the joined sub-components at least partially bond together, thus solidifying the assembled component, and in some cases increasing its density.

It should be noted that the porosity of all sub-components decreases during sintering, including that of porous sub-components. However, because the size of the space-holders in the porous sub-component are typically much larger than the binder particles that are mixed with the material powder, the portion of the assembled component that is porous maintains the void spaces from the space holders, even after sintering.

In an alternative embodiment, the porous sub-component may be both debound and sintered prior to being over-molded by the second sub-component.

Figure 11:
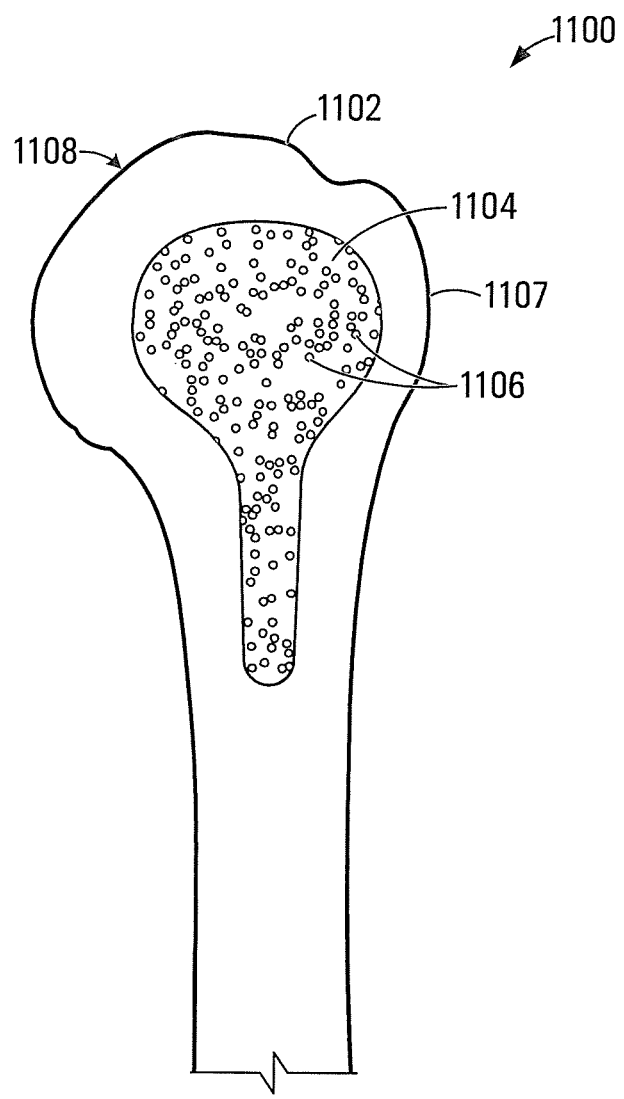
FIG. 11 shows a non-limiting example of a medical component formed via the co-processing method of FIG. 10.

Shown in FIG. 11 is a cross-sectional view of a component that can be formed according to method 3 described above. In the non-limiting example shown, the component is a medical component in the form of a bone implant 1100. The bone implant 900 includes a body portion 1108 that has a density that decreases from the peripheral surface 1107 of the body portion 1108 towards the center of the body portion. This difference in density between the center portion of the implant 1100 and the peripheral surface 1107 of the implant 1100 is achieved by overmolding a second sub-component 1102 over a more porous first sub-component 1104.

Although the medical component shown in FIG. 11 is a bone implant 1100, it should be appreciated that the medical component may be a surgical implant; such as a hip implant, or other orthopaedic implant, or could also be a surgical tool or a cutting guide, among other possibilities.

The bone implant 1100 shown in FIG. 11 comprises a body portion 1108 that is formed from a first sub-component 1104 and a second sub-component 1102. The second sub-component 1102 is overmolded over the first component 1104, such that the second sub-component 1102 surrounds the first sub-component 1104.

The first sub-component is formed from a first metal material via a metal injection molding process. The feedstock that is used to form the first sub-component 1104 comprises space-holders such that when the space holders have been removed, void spaces 1106 are left within the first sub-component 1104. In addition, small porosities (not shown) are left behind as a result of the removal of the binder material. Once the first sub-component 1104 has been sintered, both void spaces 1106 (from the removal of the space holders) and porosities (from the removal of the binder) are left within the first sub-component 1104. Due to the void spaces 1106, the first sub-component 1104 will be less dense than the second sub-component 1102. In general, the first sub-component 1104 will have a density of less than 99% of a theoretical possible density, which is the density of the same metal material in its pure form. And more specifically, the first sub-component 1104 will have a density of less than 95% of the theoretical possible density.

The second sub-component 1102 is made of a second metal material that is molded over the first sub-component 1104. Once the feedstock or the second sub-component 1102 has been debound and sintered, the space where the binder once was leaves small porosities. Given that the second sub-component 1102 does not include void spaces from any space holders, the second sub-component 1102 will be more dense than the first sub-component 1104. However, due to the porosities, the second sub-component 1102 will be less dense it would be if it was made from the same metal material in its pure form. In accordance with a non-limiting embodiment, the second sub-component 1102 has a density of less than 99% of a theoretical possible density, which is the density of the same metal material in its pure form.

The first sub-component 1104 and the second sub-component 1102 can be made of the same metal material, or different metal materials, depending on the desired performance characteristics of the finished component. Some non-limiting examples of materials that can be used for the first sub-component 1104 and the second sub-component 1102 may include stainless steel alloys, cobalt-chrome alloys, titanium, titanium alloys, alumina ceramics and cermets, as well as zirconia ceramics and cermets, among other possibilities.

In the case of the bone implant 1100 shown in FIG. 11, the second sub-component 1102 forms a relatively dense outer shell that surrounds the less dense inner center. In this manner, the second sub-component provides strength and durability characteristics to the finished bone implant 900, while the less dense first sub-component 1104 provides weight reduction.

Once the first sub-component 1104 and the second sub-component 1102 have been joined together, the finished bone implant 1100 provides a medical component that decreases in density from a peripheral surface to the center region of the component.

Although only two sub-components 1104 and 1102 have been shown in FIG. 11, it should be appreciated that multiple different sub-components could be used in order to form a medical component according to the present invention. In the case where multiple sub-components are used, that are each overmolded each other, it is possible that each sub-component may have a different density, such that when joined together to form the finished component, the decrease in density towards the center of the finished component occurs more gradually.

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A medical component comprising:
   a first portion formed of a first metal material, wherein
      the first metal material comprises a plurality of first porosities having first sizes corresponding to sizes of a first sintered binder material, and
      the first metal material has a first material density of less than 99% of a theoretical possible first material density of the first metal material without the plurality of first porosities; and
   a second portion formed of a second metal material, the second metal material being different from the first metal material, wherein
      the second metal material comprises a plurality of second porosities having second sizes corresponding to the sizes of a second sintered binder material, and a plurality of large porosities having a diameter greater than a diameter of a first porosity of the plurality of first porosities and a diameter of a second porosity of the plurality of second porosities, wherein the second metal material has a second material density of less than 99% of a theoretical possible second material density of the second metal material without the plurality of second porosities and the plurality of large porosities;

the first portion and the second portion are joined together at a region of interface, wherein the region of interface between the first portion and the second portion is substantially seamless, and the first portion and the second portion are formed separately.

2. A medical component comprising:

a first portion formed of a first metal material, the first portion having a first interior wall defining a first recess, wherein the first metal material comprises a plurality of first porosities having first sizes corresponding to sizes of a first sintered binder material, and the first metal material has a first material density of less than 99% of a non-porous first material density of the first metal material without the plurality of first porosities; and a second portion formed of a second metal material, the second portion having a second interior wall defining a second recess, wherein the second metal material comprises a plurality of second porosities having second sizes corresponding to the sizes of a second sintered binder material, wherein the second metal material has a second material density of less than 99% of a non-porous second material density of the second metal material without the plurality of second porosities; and the first recess and the second recess form a hollow interior region of the medical component that is fully enclosed by the first interior wall and the second interior wall.

3. The medical component of claim 2, wherein the density of the second portion is less than the density of the first portion.

4. The medical component of claim 2, wherein the first portion is formed from a first sub-component and the second portion is formed from a second sub-component, the first sub-component and the second sub-component being formed via a metal injection molding process.

5. The medical component of claim 4, wherein a feedstock from which the second sub-component is formed comprises space holders configured to provide the large porosities within the second portion.

6. The medical component of claim 2, wherein the gradation in density occurs over a region of interface between the first portion and the second portion.

7. The medical component of claim 2, wherein the second metal material of the second portion has a density of less than 97% of a theoretical possible density.

8. The medical component of claim 2, wherein the first metal material and the second metal material are the same.

9. The medical component of claim 2, wherein the first metal material and the second metal material are different metal materials.

10. The medical component of claim 2, wherein the first metal material and the second metal material each comprise at least one of a stainless steel alloy, cobalt-chrome alloy, titanium, titanium alloy, alumina ceramic, alumina cermet, zirconia ceramic and zirconia cermet.

11. The medical component of claim 2, wherein the second metal material further comprises a plurality of large porosities having a diameter greater than a diameter of a first porosity of the plurality of first porosities and greater than a diameter of a second porosity of the plurality of second porosities.

12. The medical component of claim 2, wherein the medical component comprises a gradation in density along at least one of a longitudinal axis and a transversal axis.

13. A medical component comprising:

a first portion formed of a first metal material, wherein the first metal material comprises a plurality of first porosities having first sizes corresponding to sizes of a first sintered binder material, and the first metal material has a first material density of less than 99% of a theoretical possible first material density of the first metal material without the plurality of first porosities; and a second portion formed of a second metal material, the second metal material being different from the first metal material, wherein the second metal material comprises a plurality of second porosities having second sizes corresponding to the sizes of a second sintered binder material, wherein the second metal material has a second material density of less than 99% of a theoretical possible second material density of the second metal material without the plurality of second porosities;

the first portion and the second portion are joined together at a region of interface, wherein the region of interface between the first portion and the second portion is substantially seamless, and the first portion and the second portion are formed separately.

14. The medical component of claim 13, wherein the first portion is formed from a first sub-component and the second portion is formed from a second sub-component, the first sub-component and the second sub-component being formed via a metal injection molding process, wherein the second portion further comprises a plurality of large porosities having a diameter greater than a diameter of a first porosity of the plurality of first porosities and greater than a diameter of a second porosity of the plurality of second porosities, and the density of the second portion is less than the density of the first portion.

15. The medical component of claim 13, wherein the medical component further comprises a longitudinal axis and a transversal axis, and a gradation in density exists along at least one of the longitudinal axis and the transversal axis.

* * * * *